(12) United States Patent
Okamoto

(10) Patent No.: US 6,222,935 B1
(45) Date of Patent: Apr. 24, 2001

(54) PATTERN INSPECTING METHOD AND PATTERN INSPECTING DEVICE

(75) Inventor: Shinji Okamoto, Yawata (JP)

(73) Assignee: Matsushita Electric Works, Ltd., Osaka (JP)

(*) Notice: Subject to any disclaimer, the term of this patent is extended or adjusted under 35 U.S.C. 154(b) by 0 days.

(21) Appl. No.: 09/147,709

(22) PCT Filed: Jan. 14, 1999

(86) PCT No.: PCT/JP98/02838

§ 371 Date: Feb. 22, 1999

§ 102(e) Date: Feb. 22, 1999

(87) PCT Pub. No.: WO98/59213

PCT Pub. Date: Dec. 30, 1998

(30) Foreign Application Priority Data

Jun. 25, 1997 (JP) .................................... 9-169268

(51) Int. Cl.[7] ................................................ G06K 9/00
(52) U.S. Cl. .................. 382/149; 382/147; 382/172; 382/205
(58) Field of Search .................... 382/149, 147, 382/165, 170, 181, 199, 205, 190, 194, 172, 171, 266, 274

(56) References Cited

U.S. PATENT DOCUMENTS

| | | | |
|---|---|---|---|
| 4,579,455 | * | 4/1986 | Levy et al. ............................ 356/394 |
| 4,776,022 | * | 10/1988 | Fox et al. ................................. 382/8 |
| 5,703,964 | * | 12/1997 | Menon et al. ......................... 382/170 |
| 5,872,871 | * | 2/1999 | Yokoyama et al. ................... 382/151 |
| 5,943,437 | * | 8/1999 | Sumie et al. .......................... 382/141 |
| 5,949,901 | * | 9/1999 | Nichani et al. ....................... 382/144 |

FOREIGN PATENT DOCUMENTS

| | | |
|---|---|---|
| 3-99211 | 4/1991 | (JP) . |
| 8-110940 | 4/1996 | (JP) . |
| 8-272970 | 10/1996 | (JP) . |
| 9-178442 | 7/1997 | (JP) . |

* cited by examiner

Primary Examiner—Matthew C. Bella
Assistant Examiner—Sheela Chawan
(74) Attorney, Agent, or Firm—Arent Fox Kintner Plotkin & Kahn, PLLC

(57) ABSTRACT

A pattern inspection method capable of providing an improved inspection reliability includes the following steps. A pattern classification is set every pixel-value range of a reference-image data obtained from a reference pattern. Each of the pattern classifications has reference-data preparing parameters. With respect to each pixel of the reference-image data, pixel values of a pixel window which is composed of the pixel as a center pixel and neighbor pixels around the center pixel are checked to prepare a reference data. When all of the pixels in the pixel window are within a single pixel-value range, the center pixel is decided as a pattern uniform portion, and the reference data is prepared according to the parameters of a corresponding pattern classification. When all of the pixels in the pixel window are not within the single pixel-value range, the center pixel is decided as a pattern step portion, and internal and external pattern classifications are determined, so that the reference data is prepared according to the parameters of at least one of the internal and external pattern classifications. An inspection-image data of a pattern to be inspected is compared with the reference data to detect a defect of the pattern.

15 Claims, 18 Drawing Sheets

FIG.1
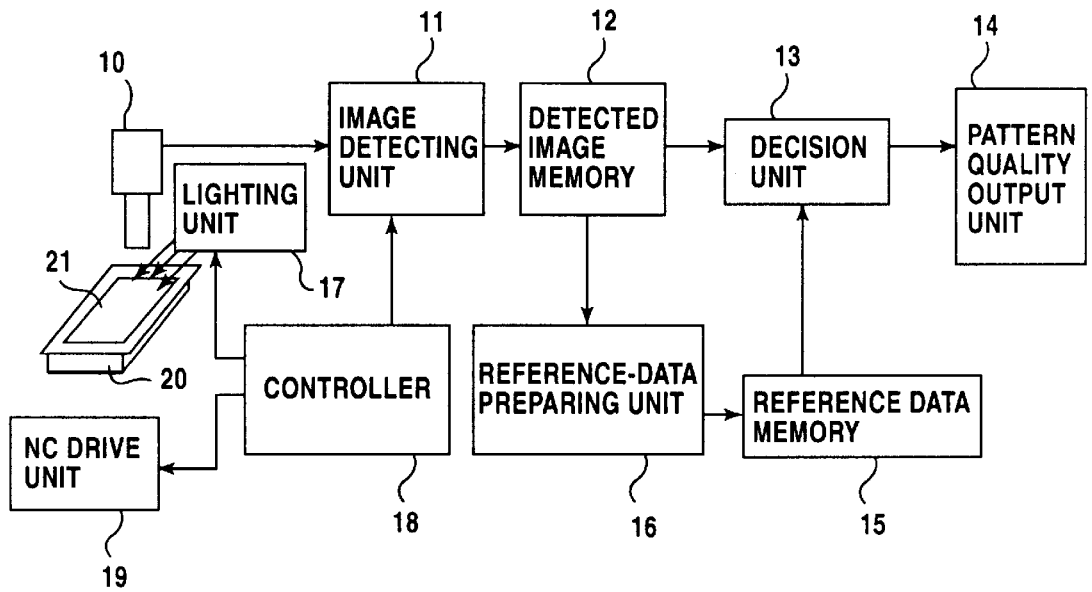
FIG.2A
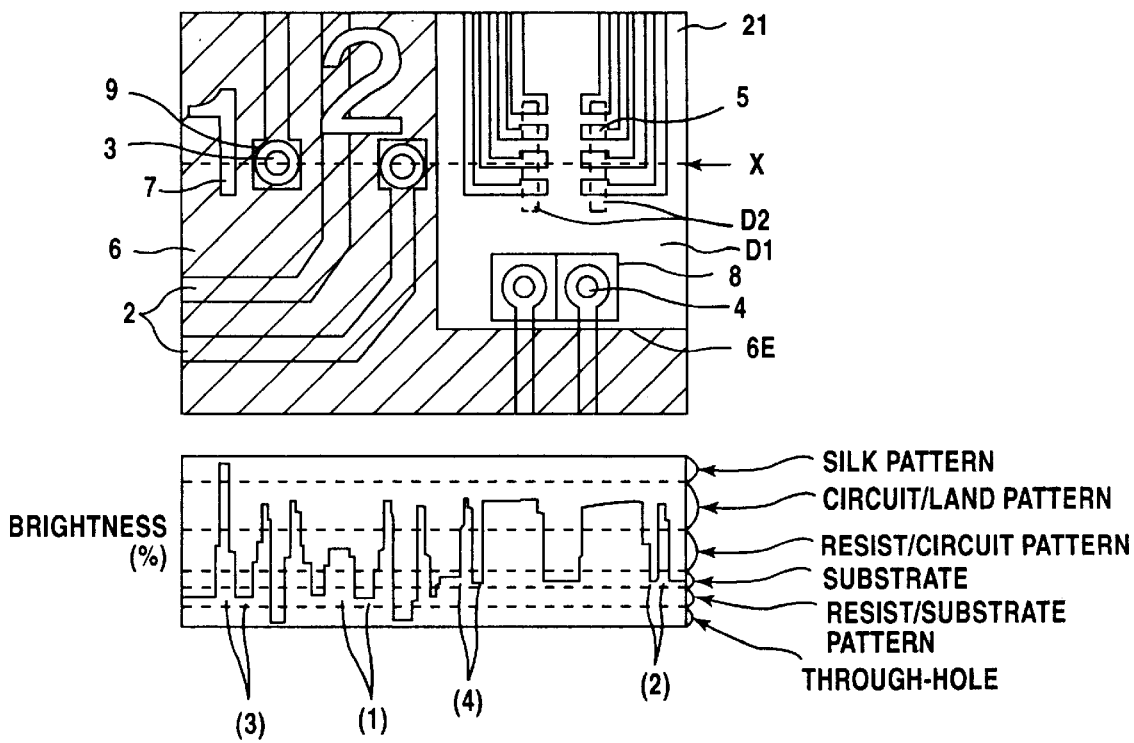
FIG.2B

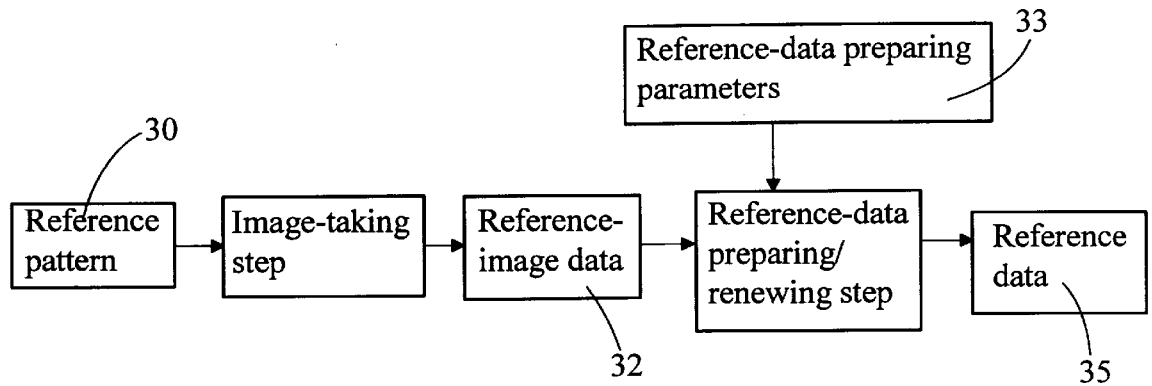
FIG. 3
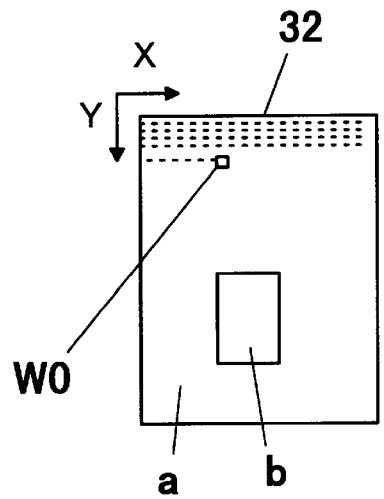
FIG. 4A
| W4 | W3 | W2 |
| --- | --- | --- |
| W | W0 (Bc0) | W1 |
| W6 | W7 | W8 |
FIG. 4B

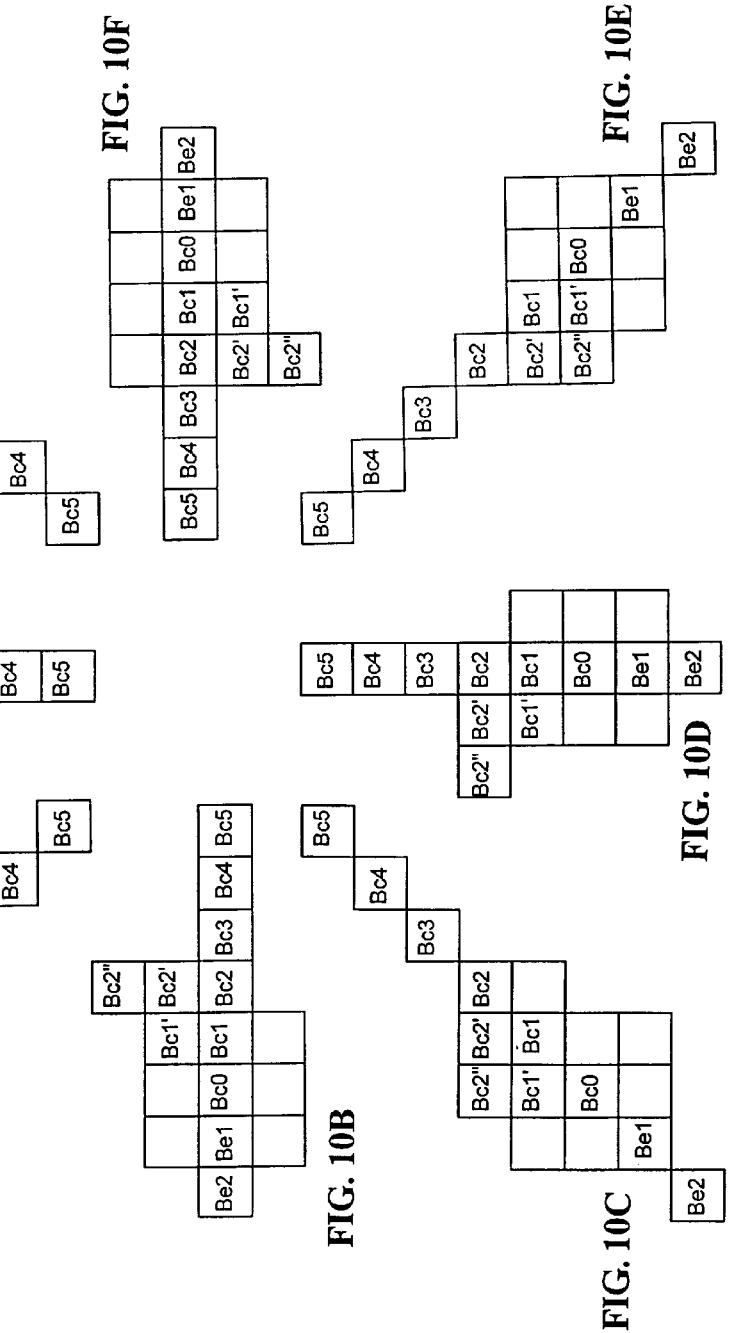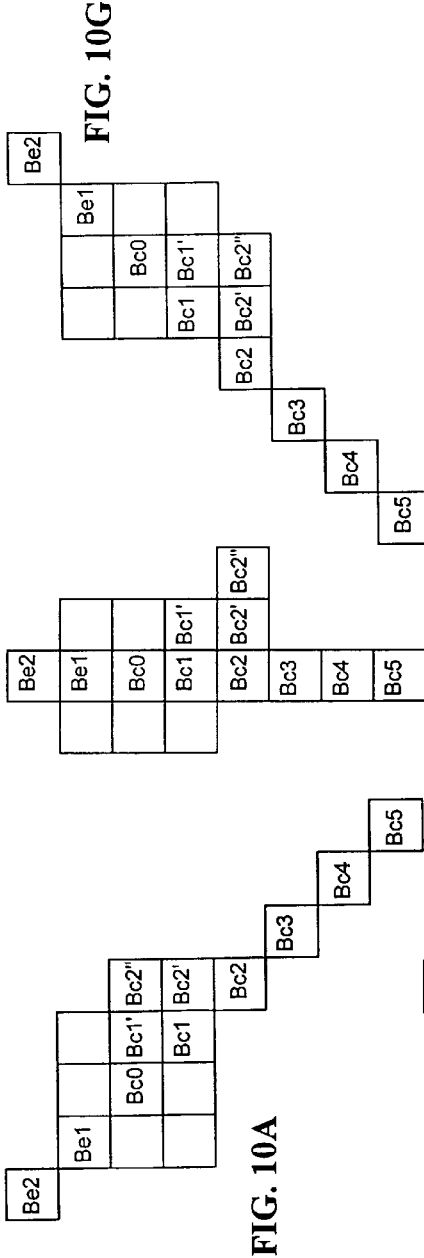

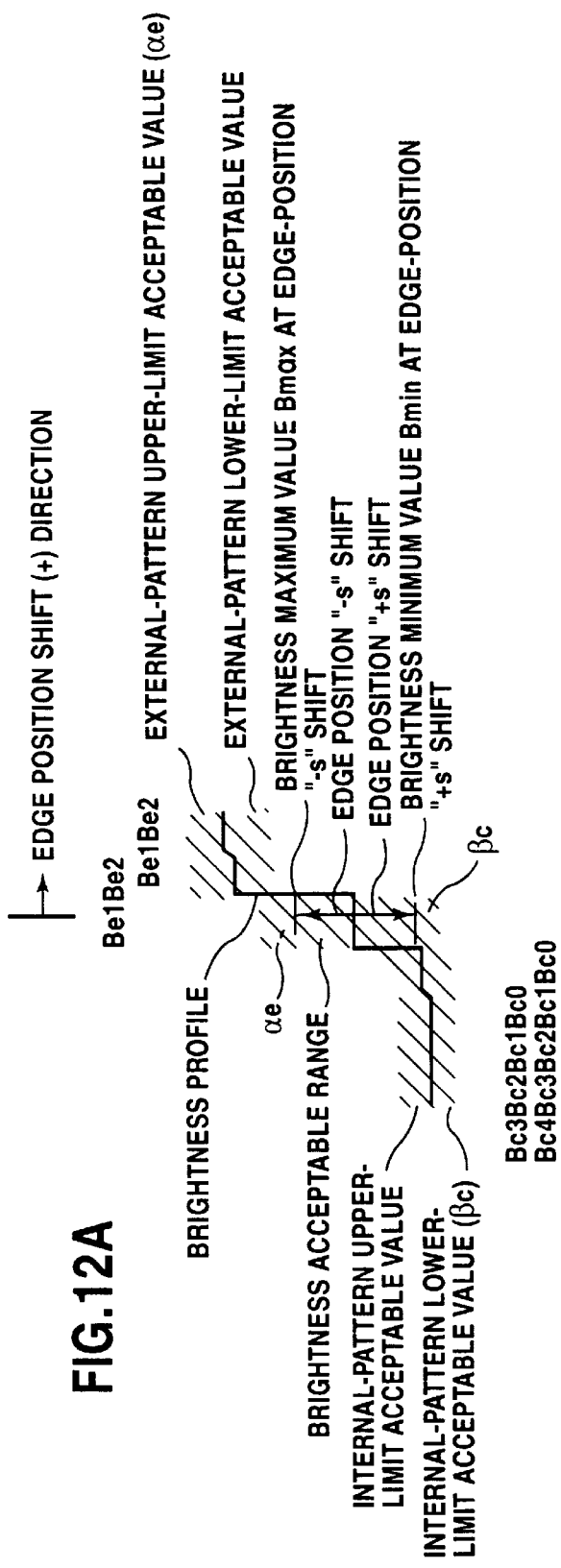
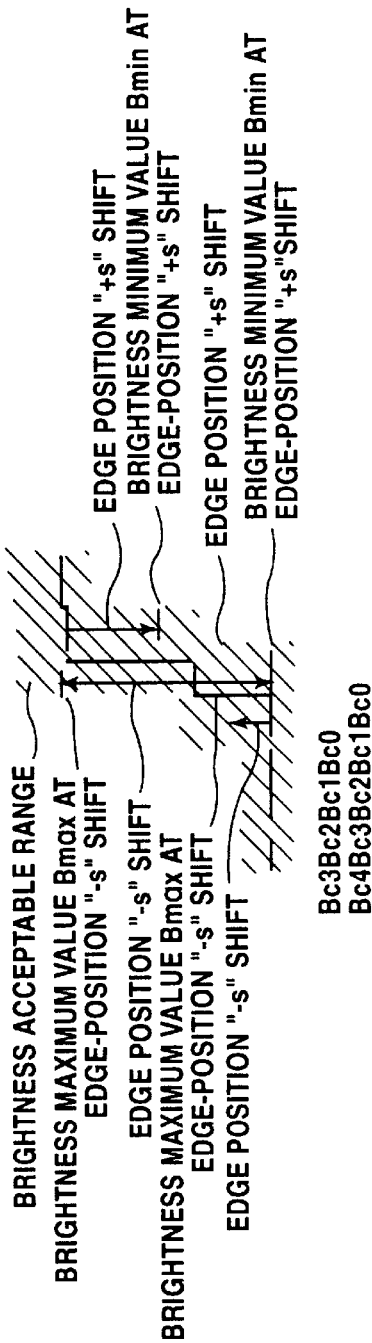
FIG.12A
FIG.12B

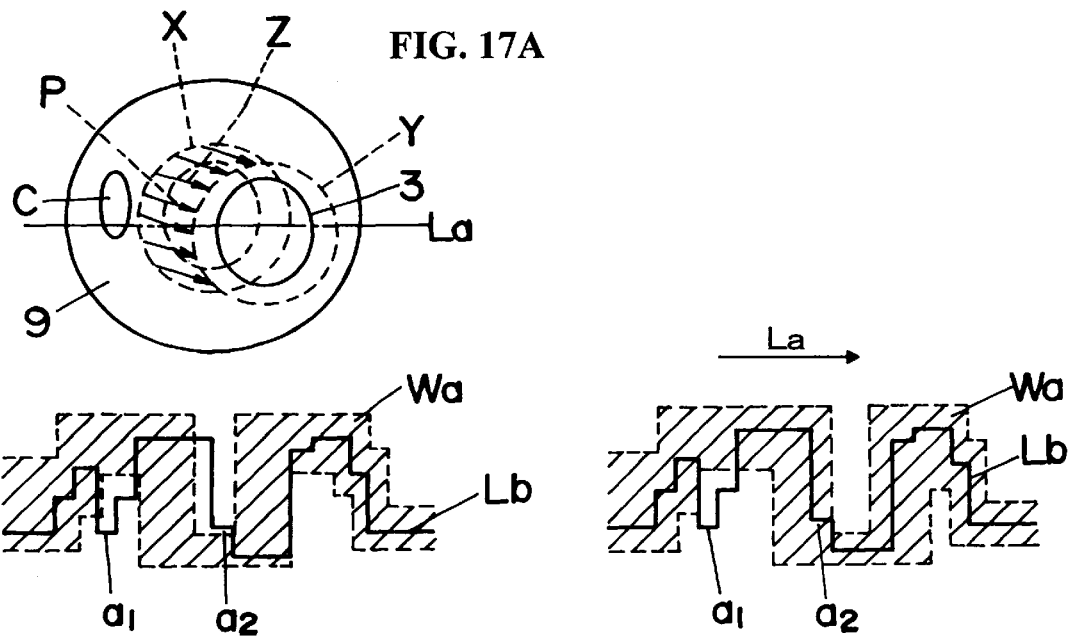
FIG. 17A
FIG. 17B
FIG. 17C
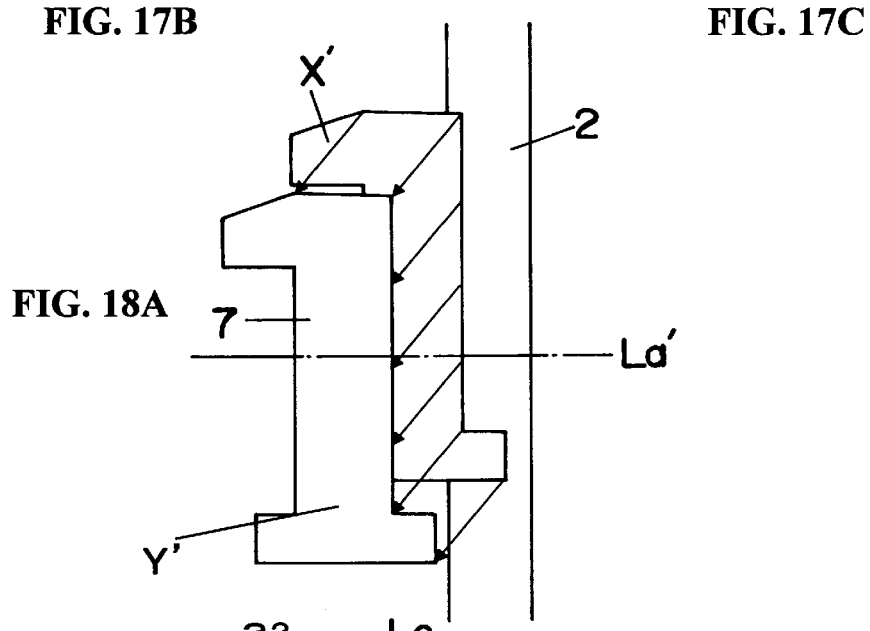
FIG. 18A
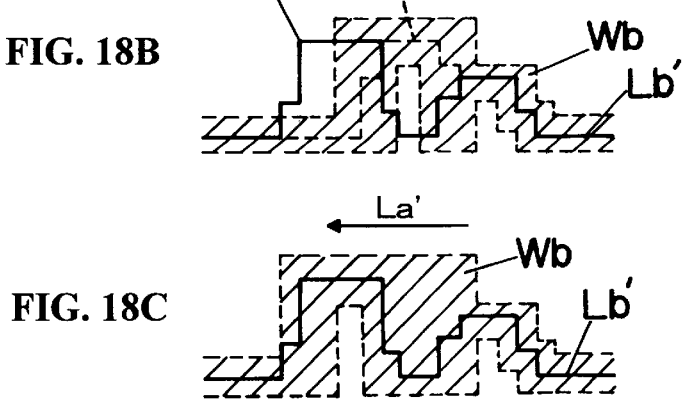
FIG. 18B
FIG. 18C

PATTERN INSPECTING METHOD AND PATTERN INSPECTING DEVICE

This is a Continuation-in-Part of International Application PCT/JP98/02838 with an international filing date of Jun. 25, 1998.

1. Field of the Invention

The present invention relates to a pattern inspection method of inspecting patterns of printed wiring boards, printed circuit boards, or the other articles with patterns, and an apparatus therefor.

2. Disclosure of the Prior Art

Printed wiring boards or printed circuit boards are usually manufactured through a plurality of manufacturing stages. As an example, a plan view of a printed wiring board is shown in FIG. 23. In a first stage, circuit patterns 2 are formed on substrates 1, and also through holes 3 or via-holes 4 are formed. In a second stage, a metal such as gold is plated on IC connecting pads 5, and solder-resist patterns 6 or silk-printing patterns (letter 7 and mark 8) are formed. In FIG. 23, the numeral 6E designates an edge of the solder-resist pattern 6.

In the first stage, defects such as short circuit, chipping, projection, pinhole, residual copper, thickening, thinning, position shift of through-hole, and disconnection of circuit pattern are inspected. These inspections can be carried out by an automatic inspection apparatus. However, since over-detection of defects frequently occurs, confirmation is needed after the automatic inspection. Thus, there is room for further improvement of the inspection reliability.

On the other hand, in the second stage, defects such as position shift, bleeding, and blur of solder-resist pattern, position shift, bleeding and blur of silk-printing pattern, projection, contamination, roughness, adherence of extraneous substance, and chipping of pad are inspected. A visual inspection by the naked eye, or using a magnifying glass is usually performed to inspect these defects. In particular, the inspection of the pads 5 needs to find a fine defect having a size within a range of about 5 to 20 $\mu$m. For this purpose, it is preferred to perform a visual inspection by using a microscope with a magnifying power of 10 to 40. However, due to the visual inspection by human, there are problems such as a low inspection efficiency and individual variations in inspection standard.

In the past, there are various kinds of methods of automatically inspecting patterns. For example, an inspection method of a circuit pattern is disclosed in Japanese Patent Early Publication [KOKAI] No. 9-178442. In this method, a defect of a pattern to be inspected is detected according to a comparison with a reference data obtained by taking images of a plurality of reference patterns. However, since careful consideration is not given to the preparation of the reference data, it is not sufficient to provide high inspection accuracy. In addition, it is desired to provide a pattern inspection method capable of coping with the following situations.

With respect to a specific pattern classification such as circuit pattern, solder-resist pattern, or silk-printing pattern, there is a case that a large acceptable amount of position shift is set. In such case, it is needed to perform the inspection while considering the acceptable amount of position shift.

There is a case that an acceptable defect-size of solder-resist pattern is much different from the acceptable defect-size of silk-printing pattern or IC connecting pad. For example, as shown in FIG. 23, although defects A such as a projection, contamination and a chipping, of the pads 5 are very fine, they are decided as bad quality. On the other hand, since defects B such as a pinhole, residual copper and a large chipping, of the circuit pattern 2 do not come into problem with respect to circuit pattern width, they are decided as good quality. Although a defect C is a fine flaking of the solder resist pattern 6, it is decided as bad quality. In addition, the inspection accuracy may be influenced by different inspecting conditions, e.g., lighting conditions. Thus, it is needed to perform the inspection while considering the kinds of defects and the inspecting condition.

There is a case that it is desired to decide a printed article having a bright spot, in a dark large area as bad quality, and as good quality a printed article having a bright spot at an edge of a dark large area, a printed article having a bright spot in a dark small area, or a printed article having a bright spot in a large area of neutral tint.

There is a case that a configuration or position of a thin line of a specific color has important information. In such a case, it is needed to inspect a specific region according to a severe inspection standard and the other region according to an average inspection standard.

SUMMARY OF THE INVENTION

A primary object of the present invention is to provide an improved pattern inspection method, which is capable of coping with the above-explained situations. That is, the pattern inspection method includes the following steps. A plurality of pattern classifications are provided according to pixel-value ranges of a reference-image data obtained from at least one reference pattern. Reference-data preparing parameters are set every pattern classification. With respect to each of pixels of the reference-image data, values of the pixel and required neighbor pixels defined around the pixel are compared with the pixel-value ranges. When the pixel and the neighbor pixels are within a single pixel-value range, the pixel is decided as a uniform portion, and the reference data of the pixel is prepared according to the reference-data preparing parameters of the pattern classification corresponding to the single pixel-value range. When at least one of the neighbor pixels is included in a different pixel-value range from the pixel, the pixel is decided as a step portion, and internal and external pattern classifications of the step portion are determined, so that the reference data of the pixel is prepared according to the reference-data preparing parameters of at least one of the internal and external pattern classifications. Thus, the reference data of each pixel of the reference-image data is obtained. Next, an inspection-image data is obtained by taking an image of a pattern to be inspected, and then is compared with the reference data to detect a defect of the pattern. The pattern inspection method of the present invention improves the reliability of pattern inspection and prevents over-detection of defects.

In a preferred embodiment of the present invention, the pixel and the neighbor pixels are arranged in an M×M-pixel window in which "M" is an integer, and the pixel is disposed at a center of the pixel window. In particular, it is preferred that the pattern inspection method also includes a re-checking treatment of the uniform portion. In the re-checking treatment, a re-checking parameter is set every pattern classification. With respect to the pixel decided as the uniform portion by using the M×M-pixel window, the re-checking parameter corresponding to the pattern classification of the pixel is compared with the integer "M" of the M×M-pixel window. When the re-checking parameter has a larger integer "N" than the integer "M", an N×N-pixel window having the pixel as a center pixel and neighbor pixels arranged around the pixel is provided. Pixel values in the N×N-pixel window are checked to cancel the decision of the uniform portion when at least one value of the neighbor pixels of the N×N-pixel window is included in a different pixel-value range from the center pixel. This re-checking treatment improves the reliability of the decision of the uniform portion. In particular, this re-checking step is useful to prevent the occurrence of wrong inspection at the vicinity of a pattern edge of silk-printing pattern or solder-resist pattern.

It is preferred to obtain the reference-image data according to one of first and second methods, as explained below. In the first method, images of a plurality of reference patterns are taken to prepare image data. After adjusting positions of the image data, an operation for determining an intermediate value of the image data is performed every pixel to obtain the reference-image data. In the second method, images of a plurality of reference patterns are taken to prepare image data. After adjusting positions of the image data, a correlation operation of the image data is performed every partial region. A combination of the image data having a high correlation is determined as the reference-image data of the partial region. Even when it is difficult to obtain a single ideal reference pattern, it is possible to obtain an optimized reference-image data from the plurality of reference patterns by these methods. As a result, the inspection accuracy can be improved.

It is preferred that the reference data of the uniform portion is a good-quality range of pixel value included in the reference-data preparing parameters of the pattern classification, and the reference data of the step portion is obtained by determining a pixel-value maximum acceptable range of each of the pixel and the neighbor pixels according to a position-shift acceptable range of pattern edge and a good-quality range of pixel value included in the reference-data preparing parameters of at least one of the internal and external pattern classifications. In this case, it is preferred that the position-shift acceptable range is determined from at least one of internal and external pattern widths of a rectangular direction to a pattern edge measured according to the reference-data preparing parameters of at least one of the internal and external pattern classifications.

It is preferred that the reference data includes a pixel-value upper-limit reference value and a pixel-value lower-limit reference value, and a pixel value of the inspection-image data is compared with the upper-limit and lower-limit reference values to detect the defect of the pattern. In this case, it is possible to improve an inspection speed by using a simple inspection algorithm.

In addition, it is preferred that the reference-data preparing parameters comprises center-mask mode parameters having a center-mask mode value, upper-limit value and a lower limit value which are used to determine the reference data of the uniform portion, edge-mask mode parameters having a edge-mask mode value, upper-limit value and a lower-limit value which are used to determine the reference data of the step portion, and shift mode parameters having shift mode values, upper-limit acceptable value and a lower-limit acceptable value. In this case, it is also preferred that a method of preparing the reference data of the uniform portion using the center-mask mode parameters comprises at least one of a first set mode, in which the upper-limit and lower-limit values of the center-mask mode parameters are forcedly set as upper-limit and lower-limit reference values of the reference data irrespective of a previously-determined reference data, and a second set mode, in which the upper-limit and lower-limit values of the center-mask mode parameters are set as the upper-limit and lower-limit reference values of the reference data only when a range between the upper-limit and lower-limit values is larger than the range between upper-limit and lower-limit reference values of the previously-determined reference data.

In addition, it is preferred that a method of preparing the reference data of the step portion using the edge-mask mode parameters comprises a first set mode, in which the upper-limit and lower-limit values of the edge-mask mode parameters are set as upper-limit and lower-limit reference values of the reference data of the pixel decided as the step portion, and a second set mode, in which the upper-limit and lower-limit values of the edge-mask mode parameters are set as upper-limit and lower-limit reference values of the reference data of a pixel located around the pixel.

Moreover, it is preferred that a method of preparing the reference data of the step portion using the shift mode parameters comprises at least one a first shift mode, in which an edge position of the step portion is shifted by a first shifting amount of 1 pixel or more in one of positive and negative directions, and a second shift mode, in which the edge position is shifted by a second shifting amount of less than 1 pixel in one of the positive and negative directions, and wherein a range between upper-limit and lower-limit reference values of the previously-determined reference data is renewed only when the range is expanded by at least one of an upper-limit correction value defined as a sum of the upper-limit acceptable value and a maximum pixel value obtained when the edge position is shifted by one of the first and second shifting amounts in a rectangular direction to an edge line, and a lower-limit correction value defined as a difference between the lower-limit acceptable limit and a minimum pixel value obtained when the edge position is shifted by one of the first and second shifting amounts in the rectangular direction to the edge line.

In addition, it is preferred that the reference-image data is separated to a plurality of inspection regions, and the reference-data preparing parameters are set every inspection region.

In addition, it is preferred that the reference data is obtained by preparing a first reference data from a first reference-image data of a specific portion of the reference pattern detected under a first condition, preparing a second reference data from a second reference-image data of a remaining portion of the reference pattern detected under a second condition, and combining the first reference data with the second reference data.

In addition, it is preferred that the reference data of a specific region of the reference pattern has a specific-region number. In this case, when a decision of defect candidate is obtained by comparing the inspection-image data with the reference data having the specific-region number, a rechecking treatment is performed to cancel the decision of defect candidate when the inspection-image data is decided as good quality by the rechecking treatment. It is also preferred that the rechecking treatment is performed according to a pixel-value fluctuation width or a comparison with a good-quality decision pattern.

Moreover, it is preferred that the rechecking treatment is performed by shifting a portion of the reference data by a shifting amount to obtain a partially-corrected reference data, and comparing the inspection-image data with the partially corrected reference data. Alternatively, it is preferred that the rechecking treatment comprises the following steps. That is, a position shift of the inspection-image data from the reference data is detected. A partially corrected reference data is prepared by shifting a specific portion of the reference data by a shifting amount in a direction of the position shift, and setting a pixel-value acceptable width of the specific portion on a reference-data blank region caused in the reference data by the shifting. The inspection-image data is compared with the partially corrected reference data. In addition, it is preferred that the specific-region number is provided to the reference data of both of the uniform portion and the step portion with respect to a required pattern classification. These re-checking treatments are useful to perform the pattern inspection while considering acceptable position shifts of through-hole, via-hole, silk-printing pattern, and so on.

A further object of the present invention is to provide a pattern inspection apparatus comprising an image-taking unit for taking images of a reference pattern and a pattern to be inspected to provide a reference-image data and an inspection-image data; a first memory unit for storing the reference-image data and the inspection-image data; a reference-data-preparing unit for preparing a reference data from the reference-image data; a second memory unit for storing the reference data; and a defect-detecting unit for comparing the inspection-image data with the reference data to detect a defect of the pattern. The reference-data preparing unit provides a plurality of pattern classifications according to pixel-value ranges of the reference-image data, and reference-data preparing parameters every pattern classification. With respect to each of pixels of the reference-image data, the reference-data preparing unit compares values of the pixel and required neighbor pixels defined around the pixel with the pixel-value ranges. When the values of the pixel and the neighbor pixels are included in a single pixel-value range, the pixel is decided as a uniform portion, and the reference data of the pixel is prepared according to the reference-data preparing parameters of the pattern classification corresponding to the single pixel-value range. When at least one of the neighbor pixels is included in a different pixel-value range from the pixel, the pixel is decided as a step portion, and internal and external pattern classifications of the step portion are determined, so that the reference data of the pixel is prepared according to the reference-data preparing parameters of at least one of the internal and external pattern classifications.

It is preferred that the pattern inspection apparatus has a rechecking unit for providing a specific-region number to the reference data of a predetermined pattern classification, and performing a re-inspecting of the inspection-image data under a specific inspecting condition when a decision of defect is obtained by comparing the inspection-image data with the reference data having the specific-region number. In this case, there are advantages of inspecting the specific region in details, reducing over-detection of defects, and improving the inspection accuracy.

These and still other objects and advantages will become apparent from the following detail descriptions of the preferred embodiments of the invention.

BRIEF DESCRIPTION OF THE DRAWINGS

FIG. 1 is a schematic view of a pattern inspection apparatus of an embodiment of the present invention;

FIG. 2A is a plan view of a printed wiring board;

FIG. 2B is a brightness profile taken along a line X of FIG. 2A;

FIG. 3 is an explanatory view of a reference-data preparing operation of the present invention;

FIG. 4A is a schematic view of a reference-image data;

FIG. 4B shows a 3×3-pixel window used in the present invention;

FIGS. 10A to 10H are reference operators of 8 edge directions;

FIGS. 12A and 12B are brightness profiles with brightness acceptable ranges prepared by the present invention;

FIGS. 17A to 17C are explanatory views of a position correction mode A;

FIGS. 18A to 18C are explanatory views of a position correction mode B;

PREFERRED EMBODIMENTS OF THE INVENTION

Figure 5:
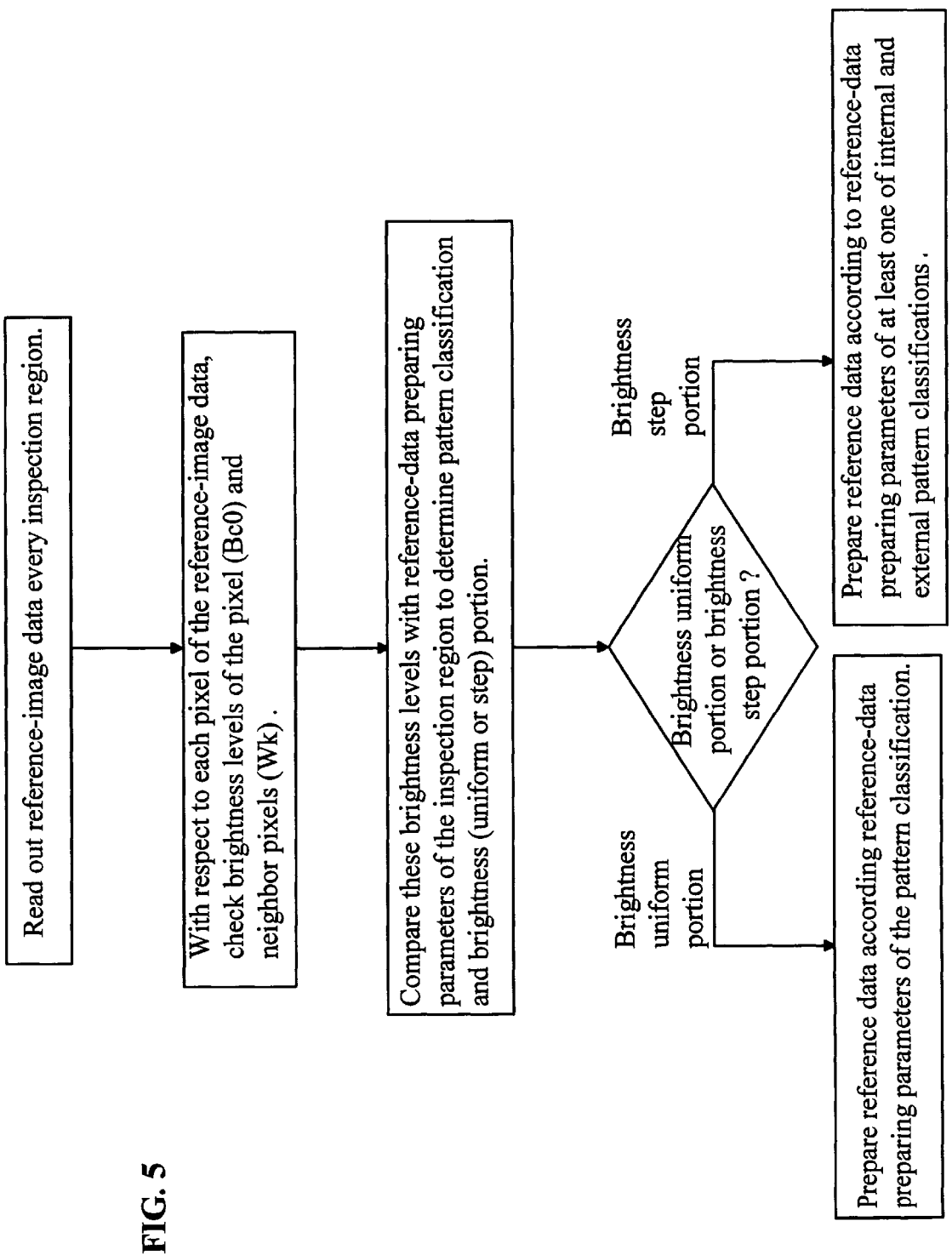
FIG. 5 is a flowchart of the reference-data preparing operation.

As shown in FIG. 1, a pattern inspection apparatus of the present invention comprises a line sensor 10, image-detecting unit 11, detected-image memory 12, decision unit 13, pattern-quality output unit 14, reference-data memory 15, reference-data preparing unit 16, lighting unit 17, controller 18 for lighting and image-taking conditions, NC drive unit 19, and a NC table 20.

A substrate 21 having a reference pattern or an inspection pattern to be inspected is placed on the NC table 20. The NC drive unit 19 is used to move the substrate 21 in a Y-axis direction in synchronization with the line sensor 10. If necessary, an XYθ-axes fine adjustment mechanism for positioning the substrate 21 may be used. The line sensor 10 can take an image of the substrate 21 on the NC table 20, while interlocking with the Y axis movement of the substrate. The lighting unit 17 provides illumination to obtain a good image of the substrate. The control unit 18 controls a switching between a single lighting unit and a plurality of lighting units, a resolution of image during the image-taking operation, and a switching of visual field. That is, the control unit 18 is needed to obtain a suitable image under various illumination and image-taking conditions, while interlocking with the image-detecting unit 11.

To perform a pattern inspection by the pattern inspection apparatus of the present invention, a reference data is firstly prepared. That is, the image-detecting unit 11 detects reference-image data by an A/D conversion of an image signal of the substrate 21 having the reference pattern. The reference-image data is stored in the image memory 12. The reference-data-preparing unit 16 generates the reference data from the reference-image data in accordance with reference-data preparing parameters. The reference data is stored in the reference-data memory 15.

A method of preparing the reference data of the present invention is explained below in details.

As shown in FIG. 2A, patterns on a wiring board 21 can be classified into a plurality of pattern classifications comprising circuit patterns 2, solder resist pattern 6, silk-printing patterns of letter 7 and mark 8, through-holes 3, lands 9, IC connecting pads 5, via-holes 4 and so on. These are made of materials having different brightness. Therefore, the pattern classification can be determined according to a brightness value (%) of a detected image. For example, FIG. 2B shows a brightness profile taken along a line X of FIG. 2A. The wiring board 21 has regions ① each having a relatively large pattern width, and region ② each having a relatively small pattern width. Furthermore, there are brightness uniform portions ③ (also called as a pattern uniform portion) where the brightness is almost uniform over a distance, and brightness step portions ④ where brightness changes are observed.

In this embodiment, as shown in FIG. 3, reference-image data 32 is obtained by an image-taking operation of a reference pattern 30. The reference-image data 32 is read out every pixel, and reference data 35 of each pixel is generated in accordance with reference-data preparing parameters 33. If necessary, it is possible to renew the reference data 35 by using a plurality of reference-image data 32.

For example, as shown in FIG. 4A, the reference-image data 32 is divided into a first inspection region (a) except for the pads ("D1" of FIG. 2A), and a second inspection region (b) including the pads ("D2" of FIG. 2A), to inspect the IC connecting pads 5 according to a severe inspection standard. For example, to prepare the reference data of each pixel of the first inspection region, the reference-data preparing parameters listed in Tables 1A and 1B are used. To prepare the reference data of each pixel of the second inspection region, the reference-data preparing parameters listed in Tables 2A and 2B are used. It should be understood that the parameters of these Tables are exemplary, and the present invention is not limited to those. In this embodiment, a brightness value is used as a pixel value of each pixel. The reference data of each pixel has brightness upper-limit reference value and brightness lower-limit reference value. If necessary, a specific region number may be provided to the reference data.

TABLE 1A

| Priority rank | Pattern classification | Brightness value | | Center mask mode | | | Edge mask mode | | |
|---|---|---|---|---|---|---|---|---|---|
| | | Upper limit (%) ap | Lower Limit (%) bp | Mode MCp | Upper limit (%) MChp | Lower limit (%) MClp | Mode MEp | Upper limit (%) MEhp | Lower limit (%) MElp |
| 0 | Through-hole | 10 | 0 | 1 | 10 | 0 | 3 | 100 | 0 |
| 1 | Silk | 100 | 95 | 2 | 100 | 80 | 2 | 100 | 10 |
| 2 | Land | 95 | 75 | 1 | 95 | 65 | 0 | 0 | 0 |
| 3 | Circuit/Resist | 75 | 40 | 0 | 0 | 0 | 0 | 0 | 0 |
| 4 | Substrate/Resist | 40 | 20 | 0 | 0 | 0 | 0 | 0 | 0 |
| 5 | Substrate | 20 | 10 | 0 | 0 | 0 | 0 | 0 | 00 |

TABLE 1B

| Priority rank | Pattern classification | Shift mode | | | Upper and lower acceptable values | | Specific region number Zp | Rechecking parameter Mp |
|---|---|---|---|---|---|---|---|---|
| | | 2p S2p | 1p S1p | sp S0p | Upper limit (%) αp | Lower limit (%) βp | | |
| 0 | Through-hole | 0 | 0 | 0 | 0 | 0 | 3 | 5 |
| 1 | Silk | 0 | 0 | 0 | 0 | 0 | 4 | 5 |
| 2 | Land | 1 | 2 | 0 | 20 | 20 | — | 5 |
| 3 | Circuit/Resist | 0 | 1 | 0.5 | 15 | 15 | — | 3 |
| 4 | Substrate/Resist | 2 | 0 | 0 | 10 | 10 | 2 | 3 |
| 5 | Substrate | 2 | 0 | 0 | 7 | 7 | | 3 |

TABLE 2A

| | | Brightness value | | Center mask mode | | | Edge mask mode | | |
| --- | --- | --- | --- | --- | --- | --- | --- | --- | --- |
| Priority rank | Pattern classification | Upper limit (%) ap | Lower Limit (%) bp | Mode MCp | Upper limit (%) MChp | Lower limit (%) MClp | Mode MEp | Upper limit (%) MEhp | Lower limit (%) MElp |
| 0 | Pad | 95 | 75 | 1 | 95 | 75 | 0 | 0 | 0 |
| 1 | Substrate | 20 | 10 | 0 | 0 | 0 | 0 | 0 | 0 |

TABLE 2B

| | | Shift mode | | | Upper and lower acceptable values | | Specific | |
| --- | --- | --- | --- | --- | --- | --- | --- | --- |
| Priority rank | Pattern classification | 2p S2p | 1p S1p | sp S0p | Upper limit (%) αp | Lower limit (%) βp | region number Zp | Rechecking parameter Mp |
| 0 | Pad | 0 | 0 | 0.3 | 10 | 10 | 1 | 3 |
| 1 | Substrate | 0 | 2 | 0 | 7 | 7 | — | 3 |

The brightness upper-limit and lower-limit reference values of the reference data of each pixel are determined as follows. For example, as shown in FIG. 4A, a pixel of the first inspection region (a) of the reference-image data 32 is named as a center pixel W0. As shown in FIG. 4B, eight neighbor pixels (W1–W8) are arranged around the center pixel W0 to obtain a 3×3-pixel window. A maximum brightness value of the pixel window is defined as Wkmax. Similarly, a minimum brightness value of the pixel window is defined as Wkmin.

A brightness value Bc0 of the center pixel W0 is compared with brightness ranges listed in Table 1A which are predetermined according to the pattern classifications. For example, when the brightness value Bc0 is 80%, it is classified as land having the brightness range between an upper limit "ap" of 95% and a lower limit "bp" of 75%. In Table 1A, the item of priority rank provides an importance level of the pattern classification. As the priority rank is smaller, the importance level is higher. In this embodiment, the priority rank of the land is 2.

With respect to the neighbor pixels W1 to W8, when "bp"≦Wkmin, and Wkmax≦"ap", all of the neighbor pixels of the pixel window belong to the same pattern classification as the center pixel W0. In this case, the center pixel W0 is decided as the brightness uniform portion. When the above condition is not satisfied, the pixel window has at least one pixel belonging to out of the brightness range between "bp" and "ap". Therefore, the center pixel W0 of this case is decided as the brightness step portion. FIG. 5 shows a flowchart of the above-explained method.

Figure 6:
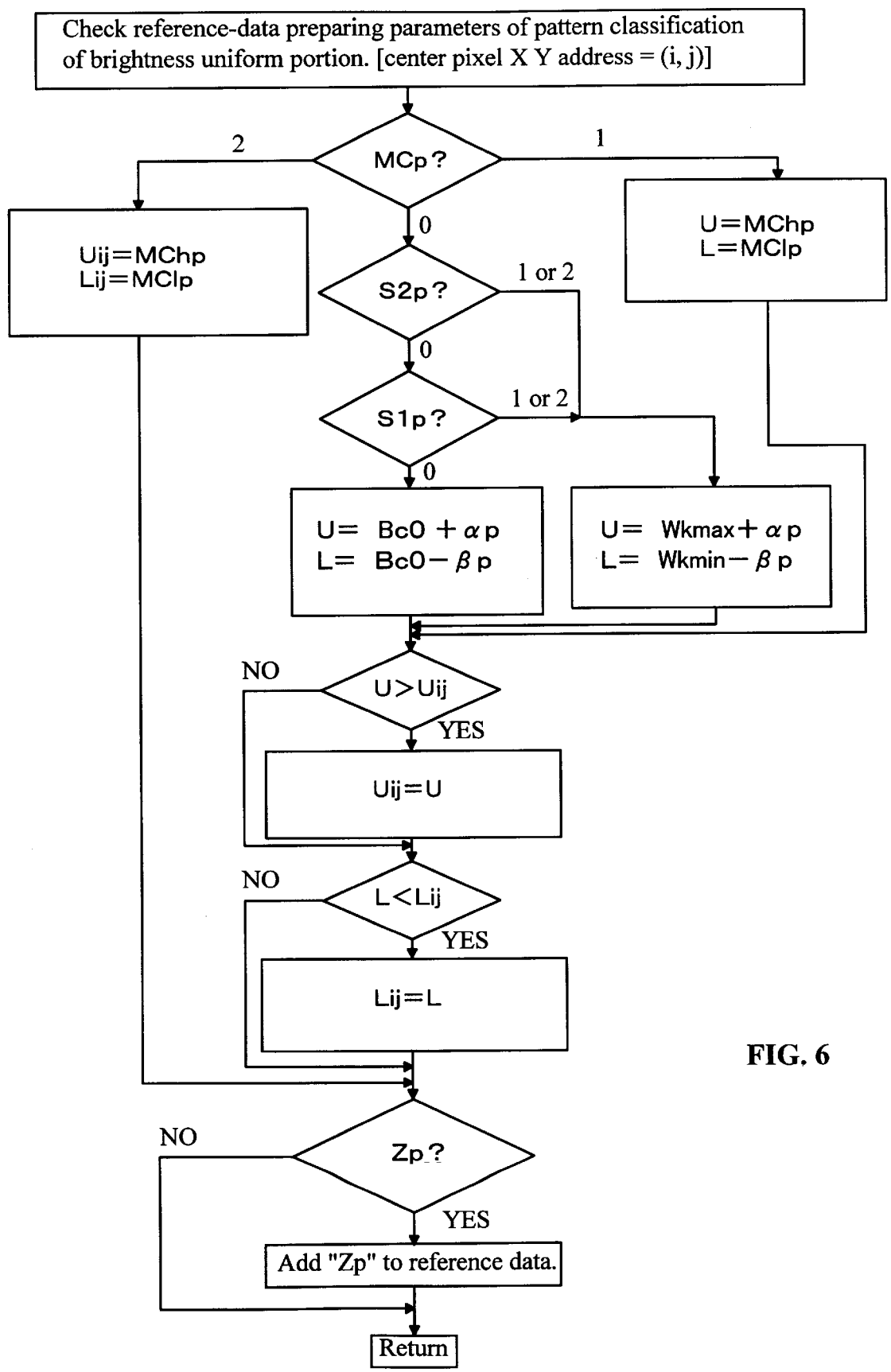
FIG. 6 is a flowchart of the reference-data preparing operation for a pixel decided as a brightness uniform portion.

Next, referring to a flowchart of FIG. 6, a method of determining a brightness upper-limit reference value "U" and a brightness lower-limit reference value "L" of the reference data of a pixel decided as the brightness uniform portion is explained. First, a center mask mode MCp, which is set every pattern classification, as listed in Table 1A, is checked. In this embodiment, one of values 0, 1 and 2 is set on the respective center mask mode. In addition, the center mask mode of each pattern classification has an upper-limit value MChp (%) and a lower-limit value MClp (%).

The reference data is prepared according to the values of MCp. That is, when MCp=2, corresponding MChp and MClp values are respectively set on the brightness upper-limit reference value "U" and the brightness lower-limit reference value "L". By the way, when preparing reference data according to an image-taking operation, there is a case that it is difficult to obtain a single reference pattern having ideal quality. In this case, a plurality of reference patterns regarded as substantially good quality are used to prepare the reference data. That is, the reference data of each pixel can be renewed according to a plurality of reference-data preparing operations using the reference patterns. When MCp=2, brightness upper-limit and lower-limit reference values (Uij, Lij) obtained at a previous reference-data preparing operation are forcedly renewed by the MChp and MClp values obtained at the next reference-data preparing operation. Thus, in this embodiment, the case of MCp=2 is named as a forced set mode.

In case of preparing the reference data of each pixel by using a single reference pattern, when MCp=1, corresponding MChp and MClp values are respectively set on the brightness upper-limit reference value "U" and the brightness lower-limit reference value "L". On the other hand, in case of preparing the reference data by using a plurality of reference patterns, only when the brightness upper-limit reference value "U" (=MChp) obtained at a reference-data preparing operation is greater than the reference value "Uij" obtained at the previous reference-data preparing operation, the brightness upper-limit reference value "Uij" is renewed to "U". Similarly, only when the brightness lower-limit reference value "L" (=MClp) obtained at a reference-data preparing operation is smaller than the reference value "Lij" obtained at the previous reference-data preparing operation, the brightness lower-limit reference value "Lij" is renewed to "L". Thus, in this embodiment, the case of MCp=1 is named as a successive set mode.

When MCp=0, the reference data is prepared according to a shift mode, an upper-limit acceptable value "αp" (%) and a lower-limit acceptable value "βp" (%), which are preset every pattern classification in Table 1B. In this embodiment, the shift mode consists of S2p, S1p and S0p. In case of preparing the reference data by using a single reference pattern, when S2p=0 and S1p=0, the brightness upper-limit reference value "U" is a sum of the brightness value Bc0 (%)

of a center pixel W0 and the upper-limit acceptable value "αp" (%) corresponding to the pattern classification of the center pixel. In addition, the brightness lower-limit reference value "L" is a difference between the brightness value Bc0 (%) of the center pixel W0 and the lower-limit acceptable value "βp" (%) corresponding to the pattern classification of the center pixel. On the other hand, in case of preparing the reference data by using a plurality of reference patterns, only when the brightness upper-limit reference value "U" obtained at a reference-data preparing operation is greater than the reference value "Uij" obtained at the previous reference-data preparing operation, the brightness upper-limit reference value "Uij" is renewed to "U". Similarly, only when the brightness lower-limit reference value "L" obtained at a reference-data preparing operation is smaller than the reference value "Lij" obtained at the previous reference-data preparing operation, the brightness lower-limit reference value "Lij" is renewed to "L".

In case of preparing the reference data by using a single reference pattern, when $S2p \neq 0$ (i.e., $S2p=1$ or 2) or $S1p \neq 0$ (i.e., $S1p=1$ or 2), the brightness upper-limit reference value "U" is a sum of a brightness maximum value Wkmax (%) of the 3×3 pixel window including the center pixel W0 and the upper-limit acceptable value "acp" (%) corresponding to the pattern classification of the center pixel. In addition, the brightness lower-limit reference value "L" is a difference between a brightness minimum value Wkmin (%) of the 3×3 pixel window and the lower-limit acceptable value "βp" (%) corresponding to the pattern classification of the center pixel. On the other hand, in case of preparing the reference data by using a plurality of reference patterns, only when the brightness upper-limit reference value "U" obtained at a reference-data preparing operation is greater than the reference value "Uij" obtained at the previous reference-data preparing operation, the brightness upper-limit reference value "Uij" is renewed to "U". Similarly, only when the brightness lower-limit reference value "L" obtained at a reference-data preparing operation is smaller than the reference value "Lij" obtained at the previous reference-data preparing operation, the brightness lower-limit reference value "Lij" is renewed to "L".

According to the above-explained manner, the brightness upper-limit and lower-limit reference values of the reference data of the center pixel decided as the brightness uniform portion could be determined. When the pattern classification of the center pixel has a specific region number "Zp", as listed in Table 1B, the specific reference number "Zp" is added to the reference data.

Figure 7:
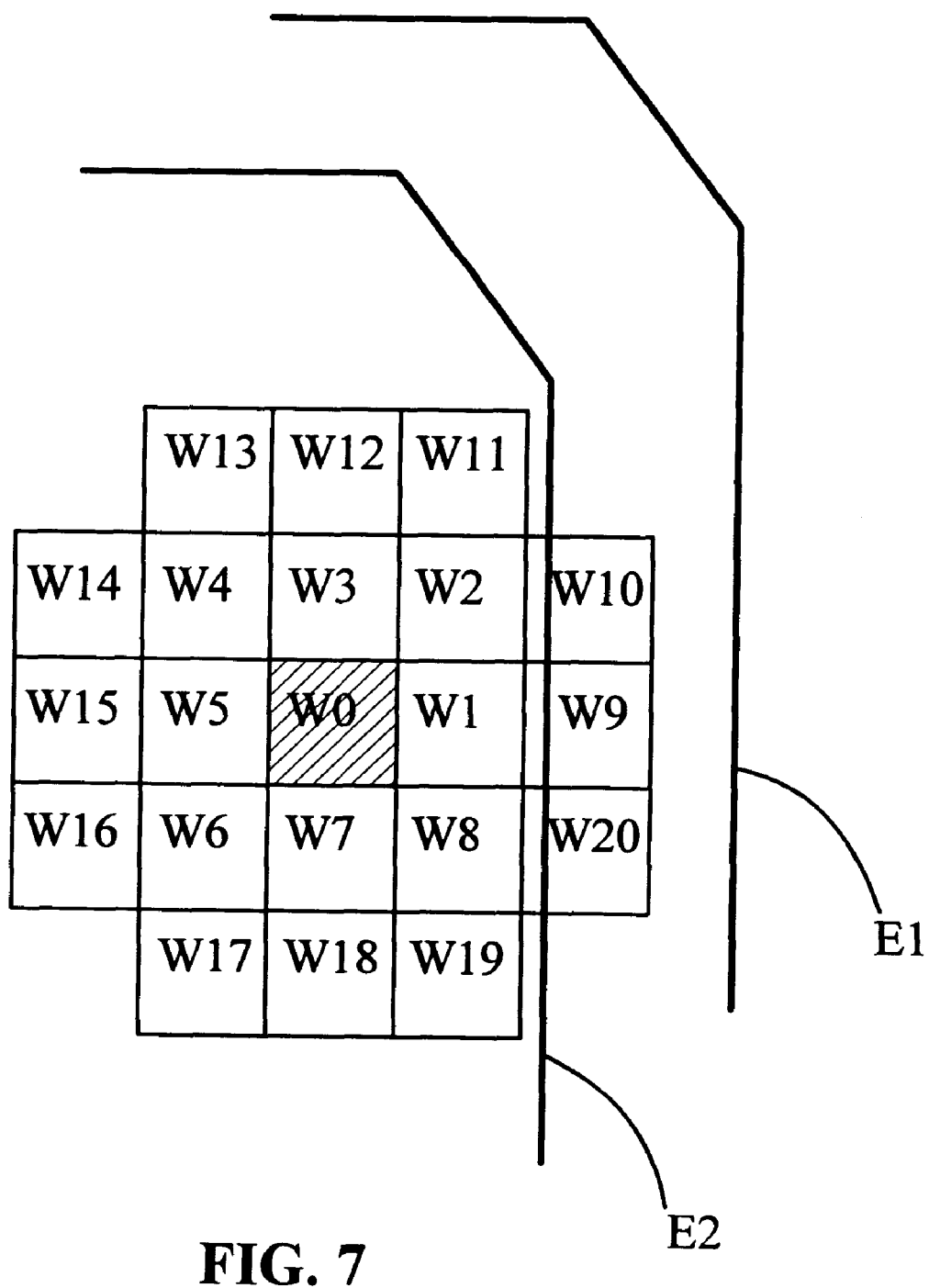
FIG. 7 is a schematic view of a 5×5-pixel window used in the present invention.

By the way, when a center pixel W0 of the 3×3 pixel window decided as the brightness uniform portion is positioned at a region close to a brightness step portion such as a pattern edge, there is a case that a relatively large brightness change within the brightness acceptable range occurs in the pixel window. In such a case, when a little severer inspection is desired, the decision of the brightness uniform portion of the center pixel can be cancelled according to the following method. That is, when the center pixel is decided as the brightness uniform portion by using the 3×3-pixel window, a larger pixel window including the 3×3-pixel window is provided. As shown in FIG. 7, the larger pixel window substantially has a 5×5-pixel arrangement except that four pixels of corners of the 5×5-pixel arrangement are not used. Therefore, 21 pixels are arranged in the larger pixel window.

A brightness maximum value W2kmax and a brightness minimum value W2kmin of the larger pixel window are checked. When W2kmin ≦ a lower limit "bp" corresponding to the pattern classification of the center pixel, or an upper limit "ap" corresponding to the pattern classification of the center pixel ≦ W2kmax, the center pixel W0 is excluded from the brightness uniform portion. In other words, as shown in FIG. 7, when a pattern edge "E1" does not contact the larger pixel window, the decision of the brightness uniform portion of the center pixel W0 is maintained, and the specific region number "Zp" is added. However, when the a pattern edge "E2" contacts the larger pixel window although it does not contact the 3×3 pixel window, the center pixel is excluded from the brightness uniform portion.

Figure 8:
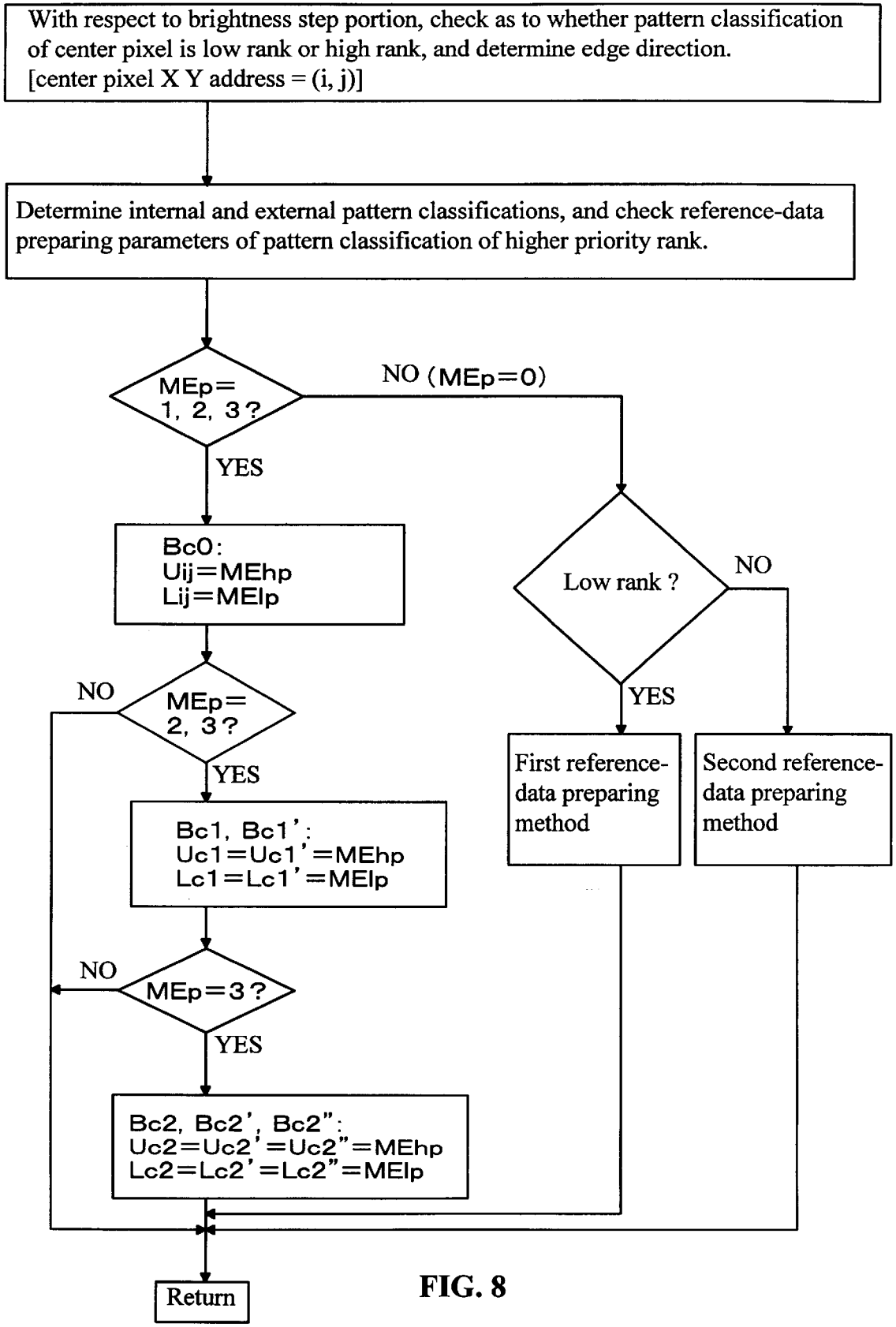
FIG. 8 is a flowchart of the reference-data preparing operation for a pixel decided as a brightness step portion.
Figure 9A:
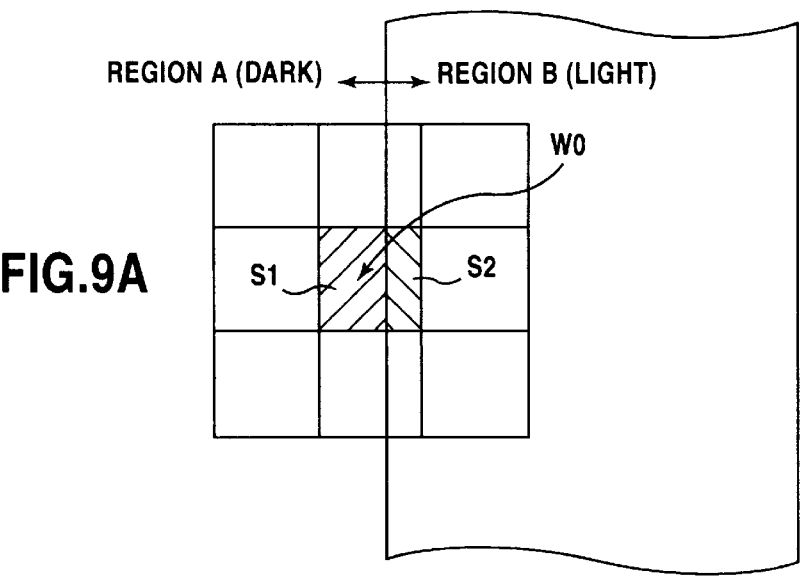
FIG. 9A is an explanatory view of an operation of checking a brightness level of a brightness step portion.

Referring to a flowchart of FIG. 8, a method of preparing reference data of a pixel decided as the brightness step portion is explained. For example, a center pixel W0 may be positioned at a pattern edge, as shown in FIG. 9A. A left side of the pattern edge is a region (A) corresponding to a pattern classification with low brightness (dark). A right side of the pattern edge is a region (B) corresponding to a pattern classification with high brightness (light). In this case, according to a ratio of an area S1 of the center pixel W0 corresponding to the region (A) and an area S2 of the center pixel W0 corresponding to the region (B), a decision as to whether the center pixel W0 is a high rank or a low rank with respect to brightness is made. For example, when the area S1 is equal to or larger than the area S2, the center pixel W0 is decided as the low rank. When the area S1 is smaller than the area S2, the center pixel W0 is decided as the high rank.

Figure 9B:
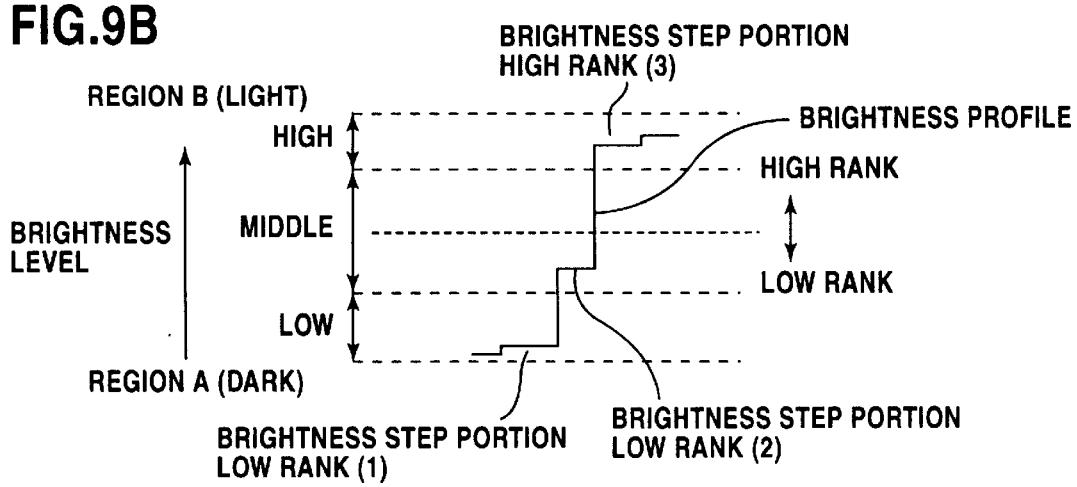
FIGS. 9B and 9C are brightness profiles explaining the checking operation.
Figure 9C:
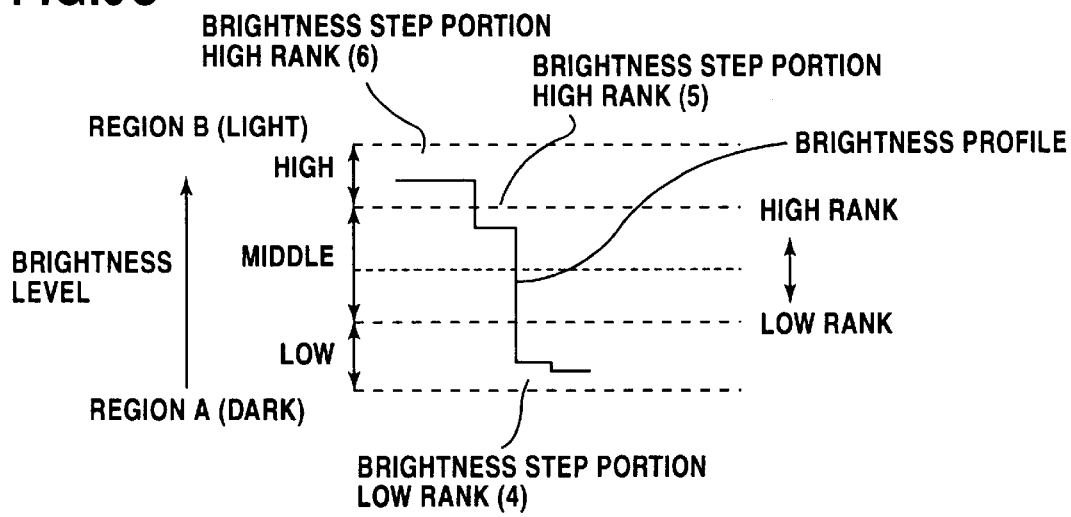

For example, in a brightness profile shown in FIG. 9B, since a brightness step portion ① is in a low brightness level, it is decided as the low rank. Since a brightness step portion ② is within a middle brightness level and closer to the low brightness level, it is also decided as the low rank. Since a brightness step portion ③ is in a high brightness level, it is decided as the high rank. On the other hand, in a brightness profile shown in FIG. 9C, since a brightness step portion ④ is in a low brightness level, it is decided as the low rank. Since a brightness step portion ⑤ is within a middle brightness level and closer to a high brightness level, it is decided as the high rank. In addition, since a brightness step portion ⑥ is in a high brightness level, it is also decided as the high rank. Thus, the high rank or low rank of the pattern classification of the center pixel W0 is firstly decided.

For example, when the center pixel W0 is decided as the low rank with respect to brightness level, a pixel providing a maximum brightness value is searched from the 3×3 pixel window including the center pixel. A direction from the center pixel to the pixel having the maximum brightness value is defined as an edge direction. Therefore, there are eight different edge directions around the center pixel. In each of the edge directions, a frame pattern, which is called as a reference operator in the technical field of image processing is predetermined, as shown in FIGS. 10A to 10H. Each of reference operators consists of center pixel Bc0 (=W0), Bc1, Bc1', Bc2, Bc2', Bc2", Bc3, Bc4 and Bc5, which are called as center-side pixels, and Be1, Be2, which are called as edge-side pixels. When determining the edge direction, it is preferred to slightly increase a weight coefficient of a pixel in a rectangular direction compared with the pixel in an oblique direction, to accurately determine the edge direction. For example, 10% to 20% of a difference between the maximum and minimum brightness values of the pixel window are suitable to the weight coefficient.

After the edge direction is determined, a minimum brightness value is searched from the center pixel Bc0 and the center-side pixels Bc1 and Bc2 of the reference operator of the edge direction. Then, a pattern classification corresponding to the minimum brightness value is determined. This pattern classification is defined as an internal pattern classification. On the other hand, a maximum brightness value is searched from the edge-side pixels Be1 and Be2 of the reference operator of the edge direction. Then, a pattern classification corresponding to the maximum brightness value is determined. This pattern classification is defined as an external pattern classification. The internal pattern classification is compared with the external pattern classification, so that a pattern classification having a higher priority rank is defined as a high-rank pattern classification.

Next, an edge mask mode MEp of the reference-data preparing parameters corresponding to the high-rank pattern classification is checked.

The edge mask mode of each pattern classification has an upper-limit value MEhp (%) and a lower-limit value MElp (%). In Table 1A, values of "0", "2" and "3" are used in the edge mask mode MEp. However, a value of "1" can be also used in the edge mask mode MEp. Therefore, the reference-data preparing operation is explained below with respect to each of the values "0", "1", "2" and "3" of the edge mask mode MEp.

When MEp=1, the upper-limit value MEhp and lower limit value MElp corresponding to the pattern classification of the center pixel Bc0 are set on the brightness upper-limit reference value "Uij" and lower-limit reference value "Lij", respectively.

When MEp=2, the upper-limit value MEhp and lower limit value MElp corresponding to the pattern classification of the center pixel Bc0 are set on the brightness upper-limit reference value "Uij" and lower-limit reference value "Lij" of the reference data, respectively. In addition, the upper-limit value MEhp of the center pixel Bc0 is set on brightness upper-limit reference values (Uc1, Uc1') of the reference data of the pixels Bc1 and Bc1'. The lower-limit value MElp of the center pixel Bc0 is set on brightness lower-limit reference values (Lc1, Lc1') of the reference data of the pixels Bc1 and Bc1'.

When MEp=3, the upper-limit value MEhp and lower limit value MElp corresponding to the pattern classification of the center pixel Bc0 are set on the brightness upper-limit reference value "Uij" and lower-limit reference value "Lij" of the reference data, respectively. In addition, the upper-limit value MEhp of the center pixel Bc0 is set on brightness upper-limit reference values (Uc1, Uc1', Uc2, Uc2', Uc2") of the reference data of the pixels Bc1, Be1', Bc2, Bc2' and Bc2". The lower-limit value MElp of the center pixel Bc0 is set on brightness lower-limit reference values (Lc1, Lc1', Lc2, Lc2', Lc2") of the reference data of the pixels Bc1, Bc1', Bc2, Bc2' and Bc2".

When MEp=0, a check is performed as to whether the pattern classification of the center pixel Bc0 is the low rank or the high rank. When the pattern classification is decided as the low rank, the brightness upper-limit and lower-limit reference values of the reference data are determined according to a first reference-data preparing method. On the other hand, when the pattern classification is decided as the high rank, the brightness upper-limit and lower-limit reference values of the reference data are determined according to a second reference-data preparing method. In each of the first and second methods, a shift mode, upper-limit acceptable value "αp" (%) and a lower-limit acceptable value "βp" (%), which are predetermined every pattern classification, are used.

Figure 11:
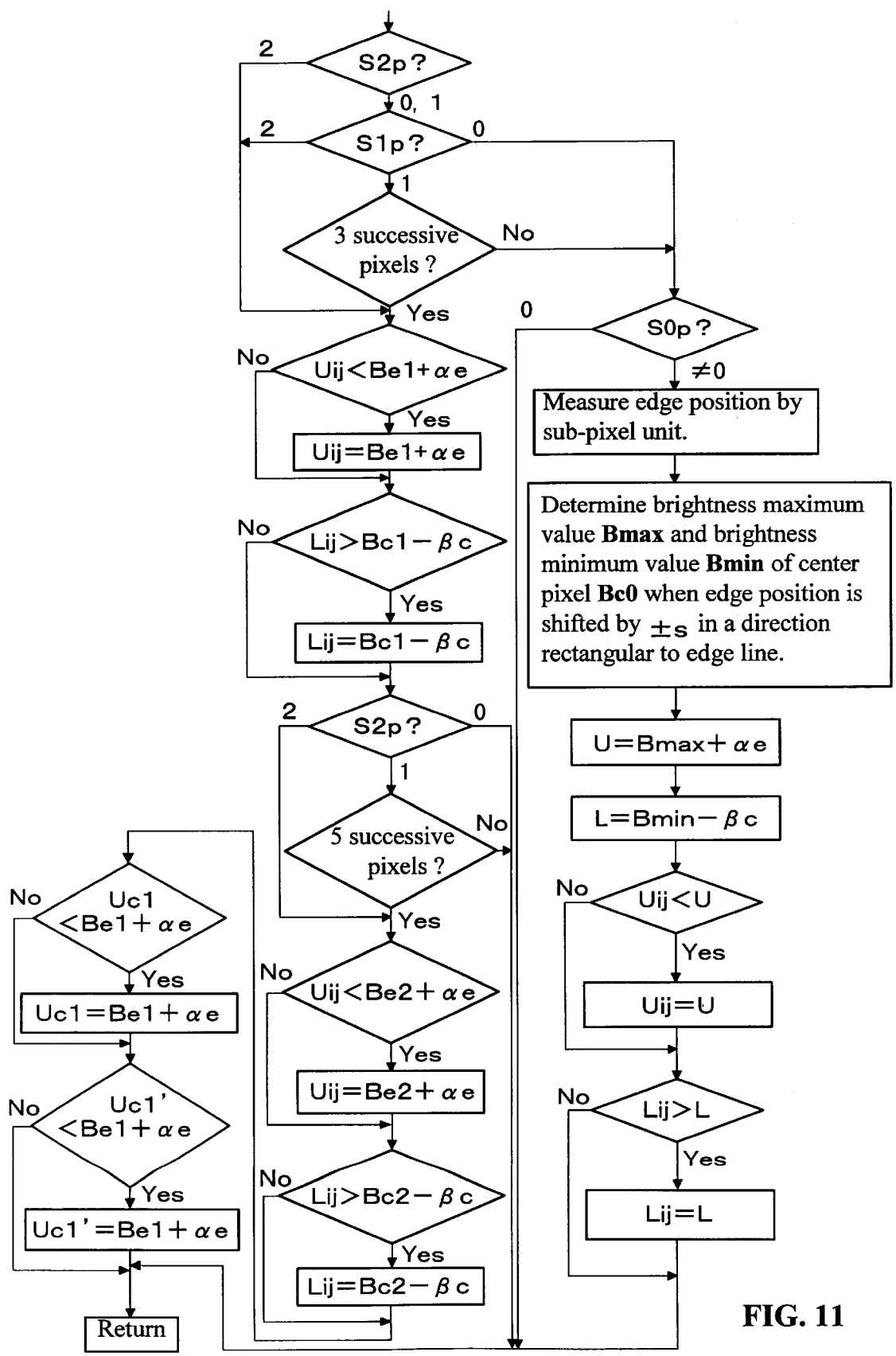
FIG. 11 is a flowchart of a first reference-data preparing method.

Referring to a flowchart of FIG. 11, the first reference-data preparing method is explained in detail.

At a first stage, when S2p=2, or S1p=2, or S1p=1 and all of the center pixel Bc0 and the center-side pixels Bc2 and Bc3 of the reference operator belong to the same pattern classification (i.e., three successive pixels), a sum of a brightness value (%) of the pixel Be1 and an external-pattern upper-limit acceptable value "αe" (%) (=an upper-limit acceptable value αp (%) corresponding to the external pattern classification) is compared with the brightness upper-limit reference value "Uij" of the center pixel Bc0 obtained at the previous reference-data preparing operation. When the brightness value (%) of the pixel Be1+αe (%)>Uij, the brightness upper-limit reference value "Uij" is renewed to Be1+αe (%). In addition, a difference between a brightness value (%) of the pixel Bc1 and an internal-pattern lower-limit acceptable value "βc" (%) (=a lower-limit acceptable value βp (%) corresponding to the internal pattern classification) is compared with the brightness lower-limit reference value "Lij" of the center pixel Bc0 obtained at the previous reference-data preparing operation. When the brightness value (%) of the pixel Bc1−βc (%)<Lij, the brightness lower-limit reference value "Lij" is renewed to Bc1−βc (%).

At a second stage, when S2p=2, or S2p=1 and all of the center pixel Bc0 and the center-side pixels Bc2, Bc3, Bc4 and Bc5 of the reference operator belong to the same pattern classification (i.e., five successive pixels), a sum of a brightness value (%) of the pixel Be2 and the external-pattern upper-limit acceptable value αe (%) is compared with the brightness upper-limit reference value "Uij" of the center pixel Bc0 obtained at the previous reference-data preparing operation. When the brightness value (%) of the pixel Be2+αe (%) >"Uij", the brightness upper-limit reference value "Uij" is renewed to Be2+αe (%). In addition, a difference between a brightness value (%) of the pixel Bc2 and the internal-pattern lower-limit acceptable value βc (%) is compared with the brightness lower-limit reference value "Lij" of the center pixel Bc0 obtained at the previous reference-data preparing operation. When the brightness value (%) of the pixel Bc2−βc (%)<"Lij", the brightness lower-limit reference value "Lij" is renewed to Bc2−αc (%).

Furthermore, a brightness upper-limit reference value Uc1 of the reference data of the pixel Bc1 is compared with the brightness value (%) of the pixel Be1+αe (%). When Uc1<brightness value (%) of the pixel Be1+αe (%), the brightness upper-limit reference value Uc1 is renewed to Be1+αe (%). Additionally, a brightness upper-limit reference value Uc1' of the reference data of the pixel Bc1' is compared with the brightness value (%) of the pixel Be1+αe (%). When Uc1'<brightness value (%) of the pixel Be1+αe (%), the brightness upper-limit reference value Uc1' is renewed to Be1+αe (%). At the second stage, when S2p=0, or five pixels are not successive, the reference-data preparing operation of the next pixel is started without the above-explained renewing operations.

On the other hand, at the first stage, when S2p=0 or 1 and S1p=0, or S1p=1 and three pixels are not successive, S0p is checked. The S0p is a sub pixel value "s" within a range of 0 to 1.

In case of S0p≠0, maximum brightness value Bmax and minimum brightness value Bmin of the center pixel Bc0 of when an edge position is shifted by ±"s" pixel are calculated. The brightness upper-limit reference value "U" of the reference data of the center pixel Bc0 is a sum of the maximum brightness value Bmax and the external-pattern upper-limit acceptable value αe (%). The brightness lower-limit reference value "L" of the reference data of the center pixel Bc0 is a difference between the minimum brightness value Bmin and the internal-pattern lower-limit acceptable value βc (%). In case of preparing the reference data by using a plurality of reference patterns, when the brightness upper-limit reference value "U" of a pixel obtained at a reference-data preparing operation is greater than the reference value "Uij" of the pixel obtained at the previous reference-data preparing operation, "Uij" is renewed to "U". Similarly, when the brightness lower-limit reference value "L" of a pixel obtained at a reference-data preparing operation is smaller than the reference value "Lij" of the pixel obtained at the previous reference-data preparing operation, "Lij" is renewed to "L". When S0p=0, the reference-data preparing operation of the next pixel is started without the above-explained renewing operations.

As examples, FIGS. 12A and 12B shows brightness acceptable regions (hatching regions) obtained by the reference-data preparing operations of the present invention when S0p≠0. That is, FIG. 12A shows the brightness acceptable region obtained when an edge position is shifted by ±"s" pixel (less than 1 pixel). On the other hand, FIG. 12B shows the brightness acceptable region obtained when an edge position is shifted to an adjacent pixel by ±"s" pixel (1 pixel or more).

Figure 13A:
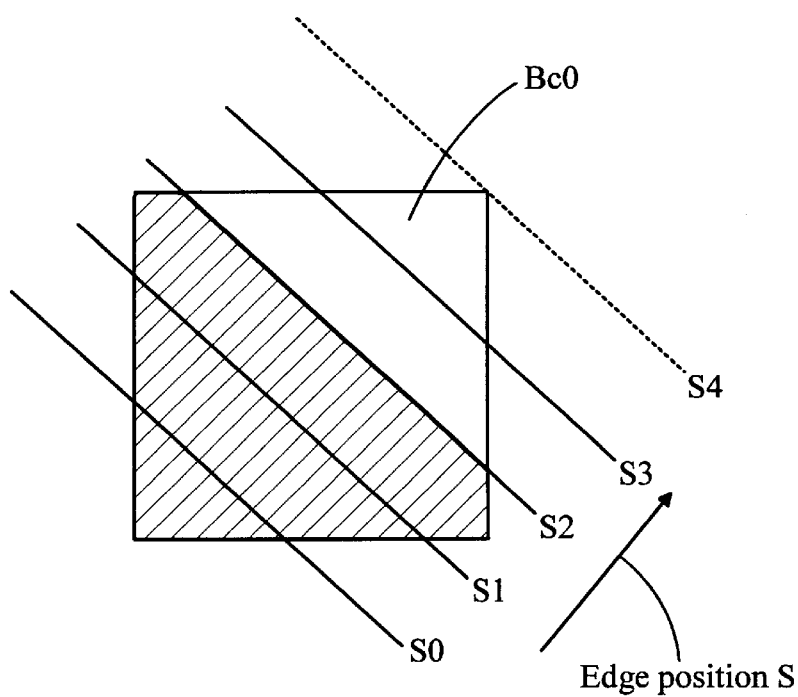
FIG. 13A is a schematic view showing oblique pattern edges extending across a center pixel.
Figure 13B:
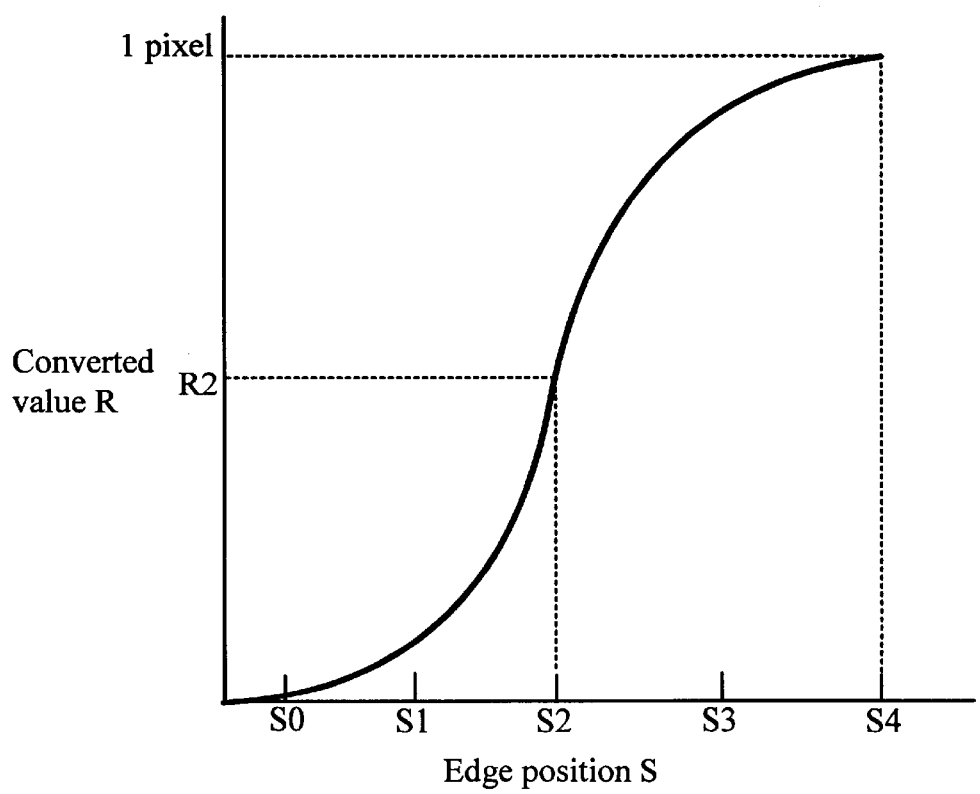
FIG. 13B is a conversion curve used to determine a brightness value of the center pixel.

By the way, there is a case that an oblique edge of a pattern extends across a center pixel Bc0, as shown in FIG. 13A. Since the pixel is of a square shape, an area (hatching area) surrounded by the oblique edge line, e.g., S2, and sides of the pixel provides brightness, which nonlinearly changes. Therefore, a converted value R corresponding to an edge position S is obtained from a conversion table, as shown in FIG. 13B. The converted value can be used to determine the brightness value of the pixel.

Figure 14:
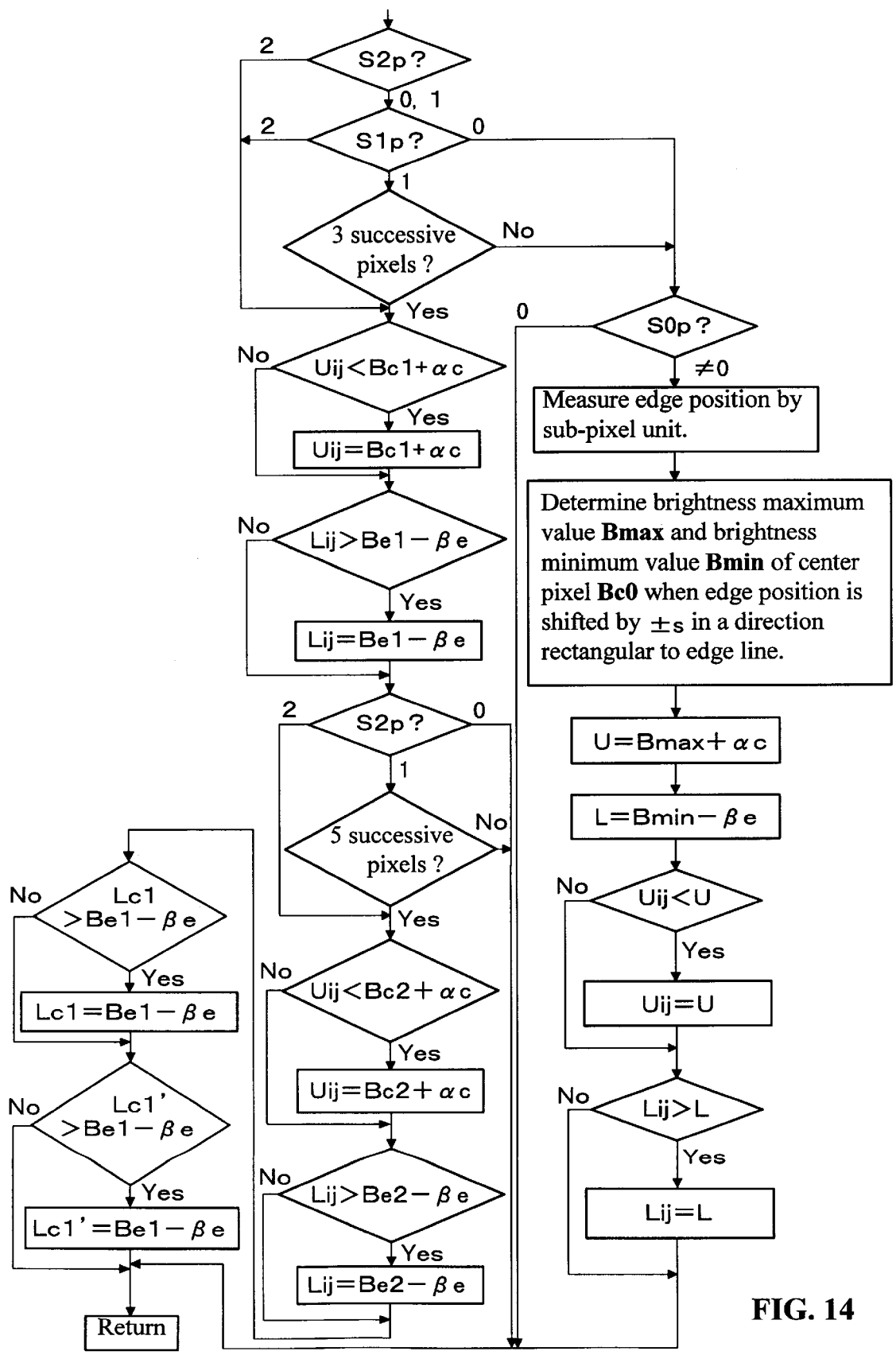
FIG. 14 is a flowchart of a second reference-data preparing method.

Referring to a flowchart of FIG. 14, the second reference-data preparing method is explained.

At a first stage, when S2p=2, or S1p=2, or S1p=1, and all of the center pixel Bc0 and the center-side pixels Bc2 and Bc3 of the reference operator belong to the same pattern classification (i.e., three successive pixels), a sum of a brightness value (%) of the pixel Bc1 and an internal-pattern upper-limit acceptable value "αc" (%) (=an upper-limit acceptable value αp (%) corresponding to the internal pattern classification) is compared with the brightness upper-limit reference value "Uij" of the center pixel Bc0 obtained at the previous reference-data preparing operation. When the brightness value (%) of the pixel Bc1+αc (%)>Uij, the brightness upper-limit reference value "Uij" is renewed to Bc1+αc (%). In addition, a difference between a brightness value (%) of the pixel Be1 and an external-pattern lower-limit acceptable value "βe" (%) (=a lower-limit acceptable value βp (%) corresponding to the external pattern classification) is compared with the brightness lower-limit reference value "Lij" of the center pixel Bc0 obtained at the previous reference-data preparing operation. When the brightness value (%) of the pixel Be1−βe (%)<Lij, the brightness lower-limit reference value "Lij" is renewed to Be1−βe (%).

At a second stage, when S2p=2, or S2p=1 and all of the center pixel Bc0 and the center-side pixels Bc2, Bc3, Bc4 and Bc5 of the reference operator belong to the same pattern classification (i.e., five successive pixels), a sum of a brightness value (%) of the pixel Bc2 and the internal-pattern upper-limit acceptable value "αc" (%) is compared with the brightness upper-limit reference value "Uij" of the center pixel Bc0 obtained at the previous reference-data preparing operation. When the brightness value (%) of the pixel Bc2+αc (%)>Uij, the brightness upper-limit reference value "Uij" is renewed to Bc2+αc (%). In addition, a difference between a brightness value (%) of the pixel Be2 and the external-pattern lower-limit acceptable value "βe" (%) is compared with the brightness lower-limit reference value "Lij" of the center pixel Bc0 obtained at the previous reference-data preparing operation. When the brightness value (%) of the pixel Be2−βe (%)<Lij, the brightness lower-limit reference value "Lij" is renewed to Be2−βe (%).

Furthermore, a brightness lower-limit reference value Lc1 of the pixel Bc1 is compared with the brightness value (%) of the pixel Be1−βe (%). When Lc1>brightness value (%) of the pixel Be1−βe (%), the brightness lower-limit reference value Lc1 is renewed to Be1−βe (%). Additionally, a brightness lower-limit reference value Le1' of the pixel Bc1' is compared with the brightness value (%) of the pixel Be1−βe (%). When Lc1'>brightness value (%) of the pixel Be1−βe (%), the brightness lower-limit reference value Lc1' is renewed to Be1−βe (%). At the second stage, when S2p=0, or S2p=1 and five pixels are not successive, the reference-data preparing operation of the next pixel is started without the above-explained renewing operations.

On the other hand, at the first stage, when S2p=0 or 1 and S1p=0, or S1p=1 and three pixels are not successive, S0p is checked. The S0p is a sub pixel value "s" within a range of 0 to 1.

In case of S0p≠0, maximum brightness value Bmax and minimum brightness value Bmin of the center pixel Bc0 of when an edge position is shifted by ±"s" pixel are calculated. The brightness upper-limit reference value "U" of the reference data of the center pixel Bc0 is a sum of the maximum brightness value Bmax and the internal-pattern upper-limit acceptable value αc (%). The brightness lower-limit reference value "L" of the reference data of the center pixel Bc0 is a difference between the minimum brightness value Bmin and the external-pattern lower-limit acceptable value βe (%). In case of preparing the reference data by using a plurality of reference patterns, when the brightness upper-limit reference value "U" of a pixel obtained at a reference-data preparing operation is greater than the reference value "Uij" of the pixel obtained at-the previous reference-data preparing operation, "Uij" is renewed to "U". Similarly, when the brightness lower-limit reference value "L" of a pixel obtained at a reference-data preparing operation is smaller than the reference value "Lij" of the pixel obtained at the previous reference-data preparing operation, "Lij" is renewed to "L".

When S0p=0, the reference-data preparing operation of the next pixel is started without the above-explained renewing operations. When S0p=0, the reference-data preparing operation of the next pixel is started without the above-explained renewing operations. In case that an oblique edge of a pattern extends across the pixel, the brightness value of the pixel can be determined by using a conversion table, as explained in the first reference-data preparing method.

Figure 15A:
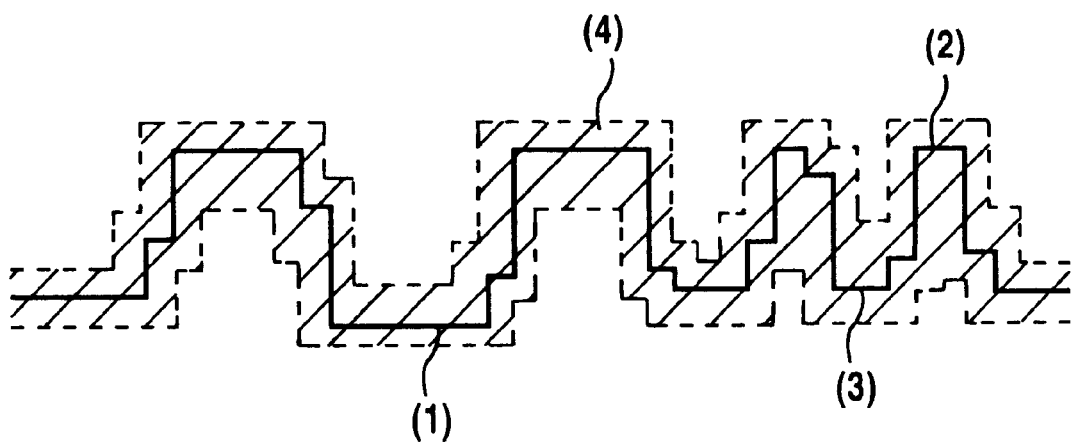
FIGS. 15A and 15B shows brightness profiles with brightness acceptable ranges prepared by the present invention.
Figure 15B:
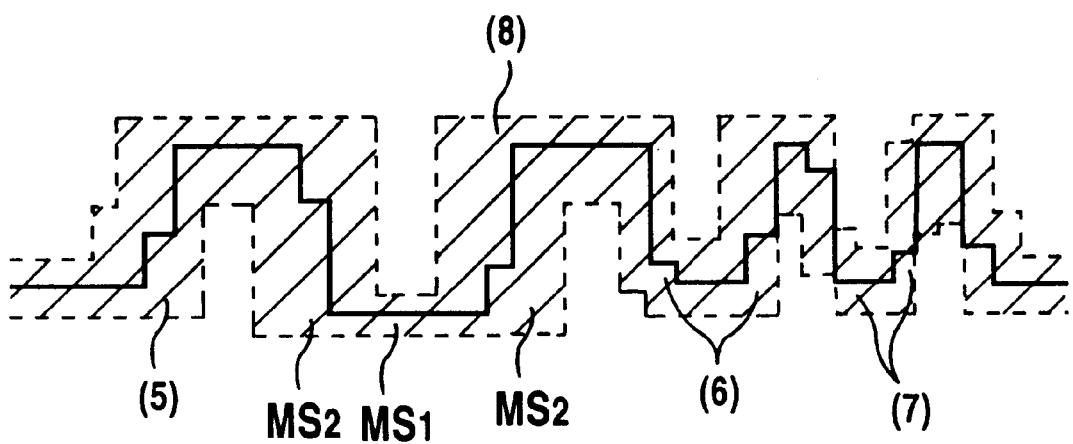

As an example, reference data prepared according to the reference-data preparing operation of the present invention are shown in FIGS. 15A and 15B. The reference data of FIG. 15A is prepared by a one-pixel forced shift under the shift mode of S1p=2. In FIG. 15A, the numeral ① designates a brightness level of a through-hole. The numeral ② designates a brightness level of a circuit pattern. The numeral ③ designates a brightness level of a substrate. The numeral ④ designates a brightness acceptable range determined according to the present invention. When a brightness profile is within the brightness acceptable range (hatching region), it is decided as good quality.

On the other hand, in FIG. 15B, the shift modes of a circuit pattern are S2p=1, S1p=1, and S0p=0.5, and with respect to through-hole, the center mask mode and 2-pixel edge mask mode are set. In FIG. 15B, the numeral ⑤ designates a large width pattern edge•2 pixel shift. That is, since the region of the numeral ⑤ has the large width, the shift mode S2p is adopted, and the brightness acceptable range is determined according to ±2 pixel-shifted positions of the edge position. The numeral ⑥ designates a middle width pattern edger•1 pixel shift. That is, since the region of the numeral ⑥ has the middle width, the shift mode S1p is adopted, and the brightness acceptable range is determined according ±1 pixel-shifted positions of the edge position. The numeral ⑦ designates a small width edge•0.5 pixel shift. That is, since the region of the numeral ⑦ has the small width, the shift mode S0p is adopted, and the brightness acceptable range is determined according to ±0.5 pixel-shifted positions of the edge position. A region MS1 is a brightness uniform portion of a through-hole, and the center mask mode is adopted. The brightness acceptable range is determined according to the upper-limit and lower-limit values of the center mask mode. A region of MS2 is a brightness step portion of the through-hole. The brightness acceptable range is determined according to upper-limit and lower-limit values of the edge mask mode over ±2 pixels. The numeral ⑧ designates a brightness acceptable range (hatching region) determined according to the present invention. When a brightness profile is within the brightness acceptable range, it is decided as good quality.

Thus, by setting the reference-data preparing parameters, it is possible to prepare the reference data for a standard inspection, as shown in FIG. 15A, and also the reference data matching inspection rules for specific objects such as pattern widths and through-holes, as shown in FIG. 15B.

Next, a quality decision of an inspection pattern to be inspected is performed using the reference data. That is, as shown in FIG. 1, the image detecting unit 11 provides an inspection image data through an A/D conversion of an image signal of the inspection pattern. The inspection image data is stored in the detected-image memory 12. The inspection image data of the detected-image memory 12 is compared with the reference data of the reference-data memory 15 by the decision unit 13 to determine the quality of the inspection pattern. The pattern-quality output unit 14 outputs information including the inspection results such as quality data, defect-position data, defect-classification data, and defect-image data.

Figure 16:
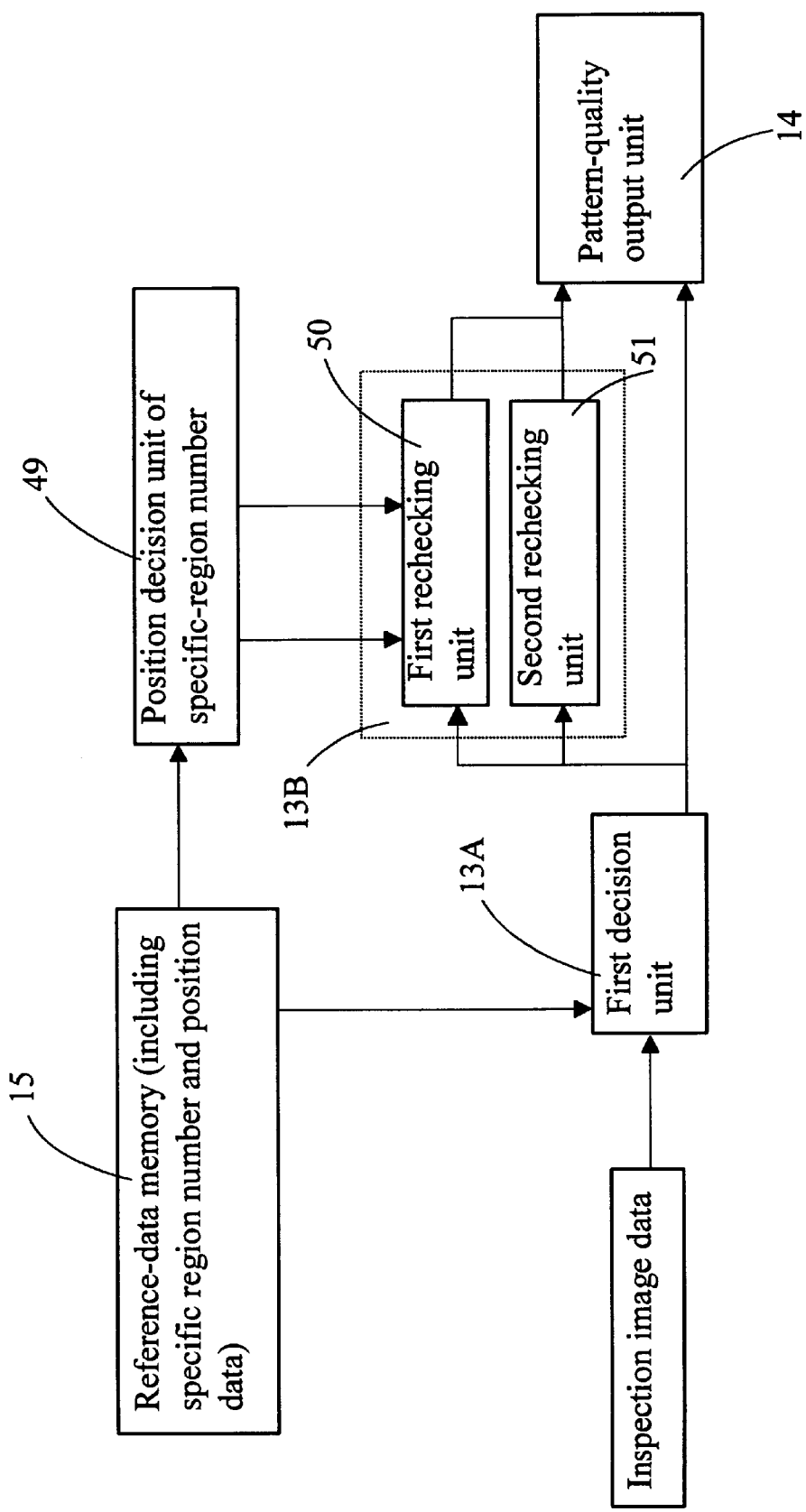
FIG. 16 is a schematic diagram of a decision unit.

As shown in FIG. 16, the decision unit 13 of this embodiment substantially consists of a first decision unit 13A and a second decision unit 13B. In the first decision unit 13A, when a brightness value of a pixel of the inspection image data is included in the brightness acceptable range between the brightness upper-limit and lower-limit reference values of the reference data of the corresponding pixel stored in the reference data memory 15, it is decided as good quality, and its information is provided to the quality-decision output unit 14. On the other hand, when the brightness value is not included in the brightness acceptable range, it is decided as a defect-candidate pixel. This defect-candidate pixel is evaluated again in the second decision unit 13B. The second decision unit 13B has a first rechecking unit 50 for the defect-candidate pixel not having the specific-region number, and a plurality of second rechecking unit 51 each of which proceeds a data treatment individual to the specific-region number.

In the first rechecking unit 50, for example, a quality-decision operation disclosed in Japanese Patent Early Publication [kokai] No.9-178442 can be performed. In brief, neighbor pixels are defined at required positions around the defect-candidate pixel. The quality decision of the defect-candidate pixel is performed using inspection image data of the neighbor pixels. When the defect-candidate pixel is decided as good quality by the first rechecking unit 50, the decision of the first decision unit 13A is cancelled. In FIG. 16, the numeral 49 designates a position decision unit of the specific-region number. In the present invention, it is possible to use a conventional method of comparing the inspection image data with the reference data to determine the quality of the inspection pattern.

On the other hand, when the reference data of the pixel corresponding to the defect-candidate pixel has the specific-region number, the second rechecking unit 51 evaluates the defect-candidate pixel again. In this embodiment, as shown in Tables 1B and 2B, the specific-region numbers "1" to "4" are given to predetermined pattern classifications. Each of the specific-region numbers has an individual data treatment, as shown in Table 3.

TABLE 3

| Specific region number | Decision mode | Decision reference value |
| --- | --- | --- |
| 1 | Brightness-fluctuation decision mode A (High frequency) | 10% |
| 2 | Brightness-fluctuation decision mode B (Low frequency) | 7% |
| 3 | Position correction mode A | 5 pixels |
| 4 | Position correction mode B | 6 pixels |

In a brightness-fluctuation decision mode A (high frequency) corresponding to the specific-region number "1", a difference between pixel values in a specific region is compared with a fluctuation reference width (for example, 10%). When the difference exceeds 10%, the pixel having the specific-region number is decided as bad quality.

In a brightness-fluctuation decision mode B (low frequency) corresponding to the specific-region number "2", an average pixel value of 7×7 pixels disposed around the center pixel is compared with a fluctuation reference width (for example, 7%). When the difference exceeds 7%, the center pixel having the specific-region number is decided as bad quality. If necessary, a brightness-fluctuation decision mode C (middle frequency) may be used to compare an average pixel value of 3×3 pixels disposed around the center pixel with a fluctuation reference width.

In a position correction mode A corresponding to the specific-region number "3", a position shift of through-hole or via hole is rechecked according to an acceptable width. For example, as shown by arrows in FIG. 17A, the rechecking operation is performed by shifting the reference data of a specific region X to a position correction region Y. In FIG. 17A, the letter C designates a pin hole, the numeral 3 designates a position of a through-hole of an inspection pattern, the numeral 9 designates a land, and the letter P designates a position of the through-hole of the reference pattern. In FIGS. 17B and 17C, a brightness profile Lb is taken along the line La of FIG. 17A. As shown in FIG. 17B, since a pin-hole portion a1 and a through-hole portion a2 of the brightness profile are not within a brightness acceptable range (hatching region), they are decided as defect-candidate portions by the first decision unit according to brightness.

However, in the position correction mode A, the brightness acceptable range corresponding to the specific region, i.e., the through-hole portion of FIG. 17B, is shifted in the direction La by a decision reference value (5 pixels in one direction), as shown in FIG. 17C. As a result, since through-hole portion a2 of the brightness profile is included in the shifted brightness acceptable range, the decision of the defect-candidate of the through-hole portion a2 is cancelled. However, since the pinhole portion a1 is still out of the shifted brightness acceptable range, the pin hole portion a1 is determined as bad quality.

By the way, although the reference data is lost at a region Z obtained by excluding the position correction region Y from the specific region X, the inspection of the region Z can be normally performed because a brightness acceptable width Wa of the specific region X is shifted and set. Thus, it is possible to perform the pattern inspection while allowing a position shift of through-hole or via-hole to some extent without lowering the pattern inspection capability.

In a position correction mode B corresponding to the specific region number "4", a position shift of silk-printing pattern such as letter and mark is rechecked according to an acceptable width. For example, as shown in FIG. 18A, the rechecking operation is performed by shifting the reference data of a specific region X' to a position correction region Y'. In FIG.1 8A, the numeral 2 designates a circuit pattern, and the numeral 7 designates a silk-printing pattern. In FIGS. 18B and 18C, a brightness profile Lb' of the inspection pattern is taken along the line La' of FIG. 18A, and a dotted line Lc designates a brightness profile of the reference data. As shown in FIG. 18B, since a brightness change portion a3 of the brightness profile Lb' caused by a position shift of the letter 7 is not included in a brightness acceptable range (hatching region), it is decided as a defect candidate portion by the first decision unit according to brightness.

However, in the position correction mode B, the brightness acceptable range of a region corresponding to the letter of FIG. 18B is shifted in the direction La' by a decision reference value (6 pixels in one direction), as shown in FIG. 18C. As a result, since the brightness change portion a3 is included in the shifted brightness acceptable range, the decision of the defect candidate is canceled and the position shift of the letter is decided as good quality.

By the way, an edge portion of the circuit pattern 2 is exposed by the position shift of the letter 7. By setting the brightness acceptable range (Wb) to such an unstable region, as shown in FIG. 18C, it is possible to prevent the occurrence of a wrong inspection of the unstable region. Thus, it is possible to perform the pattern inspection while allowing a position shift of silk-printing pattern such as letter or mark to some extent without lowering the pattern inspection capability.

When setting a pattern classification such as through holes, via-holes, or silk-printing pattern as the specific region, it is preferred to set both of the brightness uniform portion and brightness step portion of the pattern classification as the specific region. Alternatively, the specific region may be enlarged by required pixels around the brightness uniform portion. Moreover, it is possible to set the specific region in an inside direction by required pixels on the periphery of a land.

It is possible to directly input the specific region while monitoring a region to be designated as the specific region on a screen by a keyboard or mouse operation. Alternatively, it is possible to prepare a teaching pattern of this region from CAD data, take an image of the teaching pattern to teach a position of the specific region, and set upper-limit and lower-limit reference values to the reference data corresponding to the specific region, or add a specific-region number.

Alternatively, it is possible to register this region as a partial pattern having required characteristics, read reference-image data, search the partial pattern, determine the specific region according to a detected position of the partial pattern, and set upper-limit and lower-limit reference values to the reference data corresponding to the specific region, or add the specific-region number. As the required characteristics, it is preferred to use pattern configuration, brightness, chromaticity, distribution or combination of them. To search the partial pattern, it is preferred to use a pattern matching method such as a normalization correlation method.

By the way, in the pattern classification such as silk-printing pattern, land or through-hole, relatively large variations of pattern-edge positions often occur. In such a case, it is needed to decide a region separated from the pattern edges by a longer distance as the brightness uniform portion. In the present invention, it is preferred to perform a rechecking operation explained below to determine the brightness uniform portion with a higher reliability. That is, a rechecking parameter Mp is set every pattern classification, as shown in Tables 1B and 2B. First, the pattern classification of the center pixel W0 is determined using the 3×3 pixel window including the center pixel. As described above, when all of the pixels in the 3×3-pixel window are the same pattern classification, the center pixel is decided as the brightness it uniform portion.

Figure 19A:
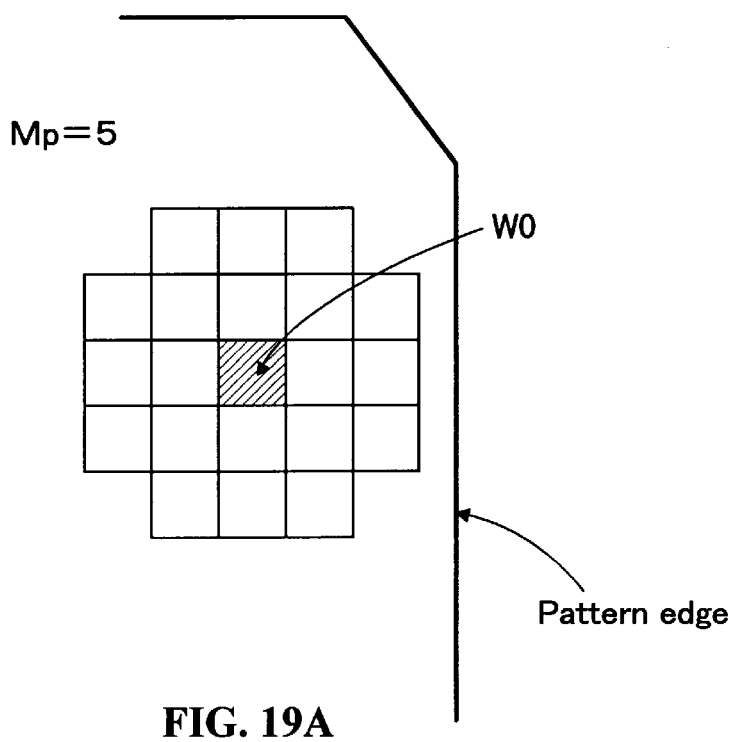
FIGS. 19A and 19B are explanatory views of an operation of rechecking a brightness uniform portion.
Figure 19B:
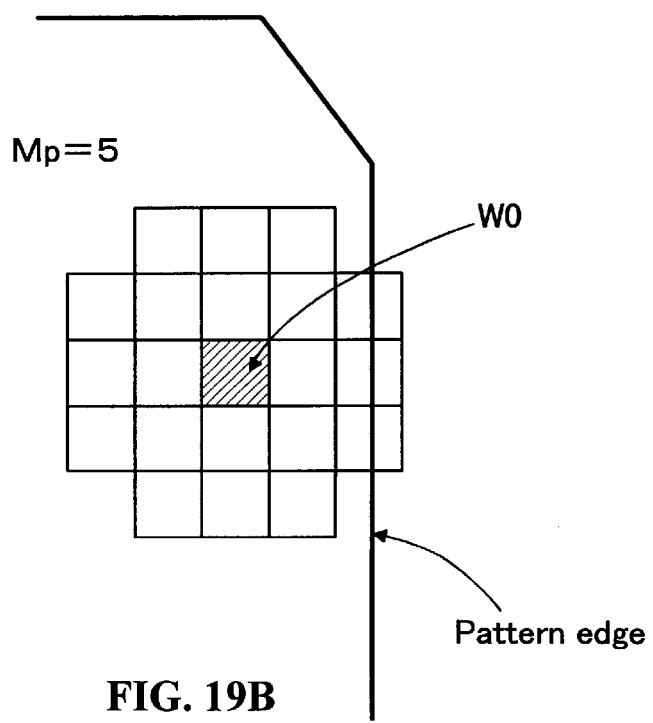

Next, the range Mp corresponding to the pattern classification of the center pixel decided as the brightness uniform portion is read out. When the range Mp is larger than 3, the above procedure is repeated using an Mp×Mp pixel window, for example, 5×5 pixel window, as shown in FIG. 19A. In the 5×5-pixel window, four corner pixels are not used because a distance from the center pixel to the corner pixel is too long. When all of the pixels in the 5×5-pixel window is the same pattern classification as the center pixel, the center pixel is decided as the brightness uniform portion. When at least one pixel in the 5×5 pixel window is different pattern classification from the center pixel, as shown in FIG. 19B, the center pixel W0 is decided as the brightness step portion, and the decision of the brightness uniform portion obtained by using the 3×3 pixel window is cancelled. Thus, the rechecking operation is useful to improve the reliability of the decision of the brightness uniform portion.

Figure 20:
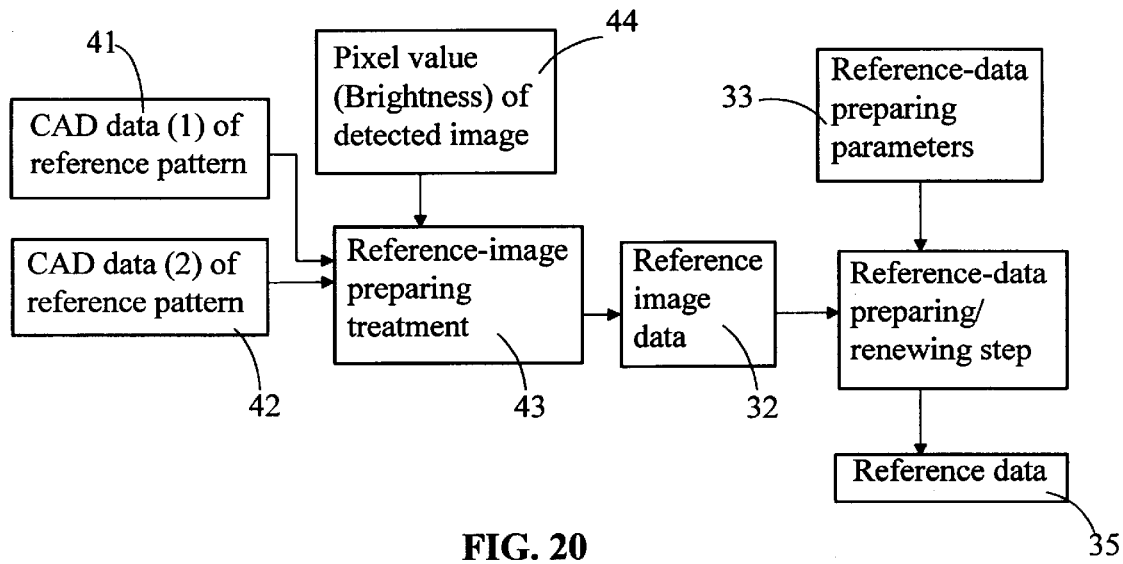
FIG. 20 is a schematic diagram showing a reference-image data preparing treatment of the present invention.

As shown in FIG. 20, the reference image data 32 can be prepared by using CAD data 41 and 42 of reference patterns. That is, a reference-image preparing treatment 43 is performed by converting, combining, and synthesizing the CAD data 41 and 42 obtained at each of manufacturing steps such as a circuit-forming step, drilling step, and a resist-printing step. In addition, information about a pixel value 44 such as brightness of detected image is added to obtain the reference-image data 32. A method of preparing the reference data 35 from the reference-image data 32 is the same as the method shown in FIG. 3. The CAD data may comprise a CAM data for manufacturing substrates.

As described above, when preparing the reference data according to the image-taking step, there is a case that it is difficult to obtain a single reference pattern having ideal quality. For such a case, the reference-image data can be prepared from a plurality of reference patterns according to the following methods.

Figure 21:
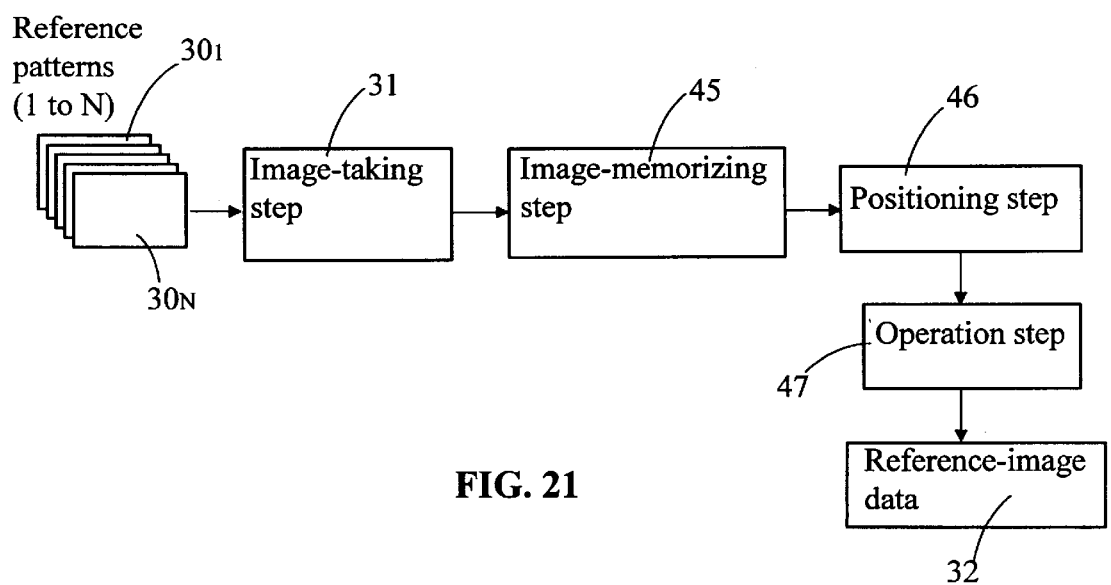
FIGS. 21 is a schematic diagram of a method of preparing a reference-image data from a plurality of reference patterns.

In a first method, as shown in FIG. 21, an image-taking step 31 of a plurality of reference patterns $30_1$ to $30_N$ is firstly performed, and images of the reference patterns are memorized 45. Next, a positioning step 46 of each reference pattern is performed, and an operation step 47 such as an intermediate-mean value operation, intermediate-value operation, or a mean-value operation of image data is performed every pixel. By avoiding unusual values and data having large variations, the reference-image data 32 is prepared. For example, by using three reference patterns, and selecting an intermediate value every pixel, it is possible to readily obtain the reference-image data. In addition, by using four or more of the reference patterns, and selecting a mean value of intermediate data except for both end data every pixel, it is possible to obtain the reference-image data with a higher accuracy.

In a second method, as shown in FIG. 21, the image-taking step 31 of the reference patterns $30_1$ to $30_N$ is performed as well as the first method, and images of the reference patterns are memorized 45. Next, a positioning step 46 of each reference pattern is performed, and a correlation operation of image data is performed every partial region as the operation step 47. A standard image data is selected from combinations of the image data having a high correlation. The selected image data is determined as the reference- image data 32 of the partial region.

In a third method, the image-taking step of the reference patterns is performed, and images of the reference patterns are memorized. Next, position shifts of the reference pattern images are measured every partial region by sub-pixel unit according to a normalization correlation method. By performing interpolation operations of neighbor pixels according to the measured position shifts, reference pattern images are obtained. From the reference pattern images, a suitable reference image data can be prepared as well as the first and second methods.

In this embodiment, brightness is used as the pixel value. However, it is possible to use a color-component value or a color-information value such as chromaticity or saturation for a color pattern inspection. Alternatively, it is possible to use a height information value as the pixel value for a three-dimensional pattern inspection. In addition, it is preferred to use a non-linearly converted value of detected image or a combined value of brightness information, color information, and height information as the pixel value.

Figure 22:
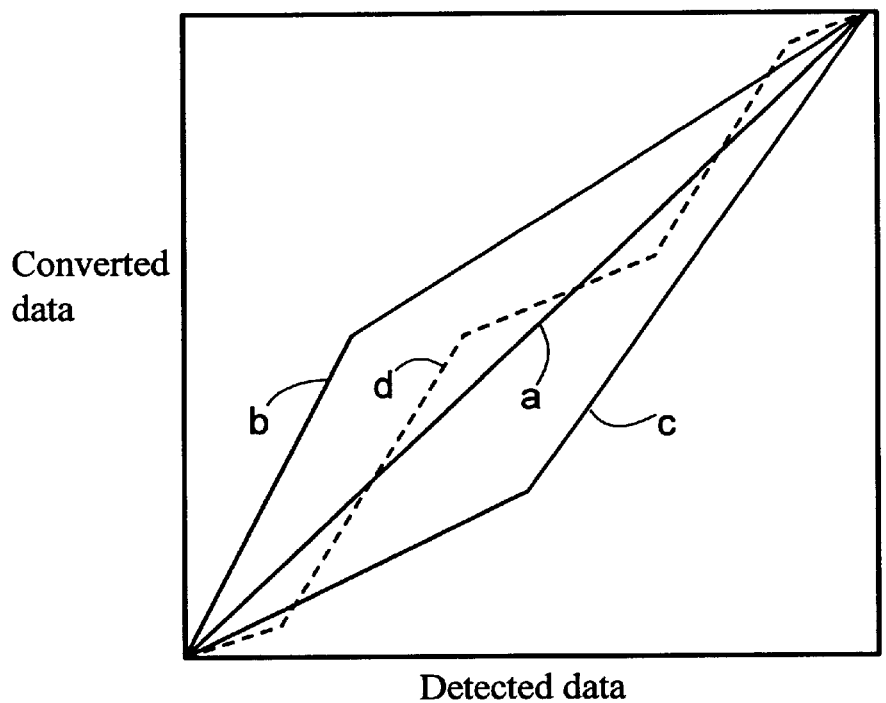
FIG. 22 is an explanatory diagram of conversion methods of detected data.
Figure 23:
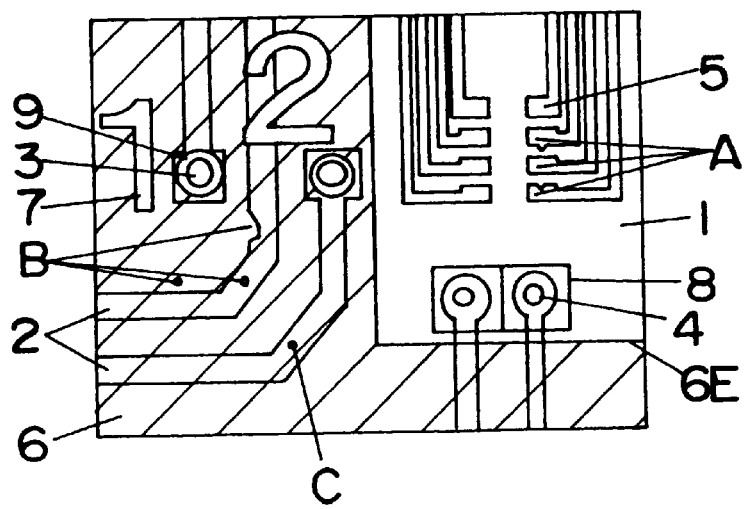
FIG. 23 is a plan view of a printed wiring board.

For example, the detected image can be converted, as shown in FIG. 22. A horizontal axis designates the detected data. A vertical axis designates a converted data. A straight line "a" shows a normal linear conversion. A polygonal line "b" shows a nonlinear conversion having a large gain at a low-pixel value portion and a small gain of a high-pixel value portion. This nonlinear conversion is useful when it is required to perform a pattern inspection by brightly detecting a circuit pattern under a solder resist, or when it is required to detect defects showing delicate brightness changes such as blur, scratch, flaking of solder resist, or adherence of extraneous substance. A polygonal line "c" shows a nonlinear conversion having a small gain at the low-pixel value portion and a large gain at the high-pixel value portion. This nonlinear conversion is useful when it is required to inspect delicate surface changes including scratch or flaking of gold plating at pad portions, stain, contamination, or adherence of extraneous substance. In addition, a dotted polygonal line "d" shows a nonlinear conversion having a plurality of gain changes. This nonlinear conversion is useful to when it is required to uniformly detect pixel value levels of various kinds of patterns and accurately detect the respective defects.

In the reference-data preparing operation of the brightness step portion of the above embodiment, one of the internal and external pattern classifications of the brightness step portion is selected according to the priority rank set every pattern classification, so that the reference-data preparing parameters of the selected pattern classification are used to prepare the reference data. Alternatively, without using the priority rank, it is possible to select the reference-data preparing parameters of one of the internal and external pattern classifications so as to provide a wider brightness acceptable range of the reference data. In addition, according to a combination of the internal and external pattern classifications, it is possible to use a predetermined pattern classification of them to prepare the reference data.

In general, as a pattern width is smaller, a narrower position-shift acceptable range is set. However, there is a case that a stable pattern width is not obtained due to variations in the manufacturing process with respect to a very thin pattern. In such a case, it is preferred to correct a reference-image data according to a pattern width on a pattern design with respect to a specific range of pattern width.

In case that the reference-image data has different pattern classifications with a same brightness level, it is preferred to set reference-data preparing parameters every inspection region with respect to the different pattern classifications.

When a brightness difference between a through-hole portion and a substrate is too small under an inspection lighting condition, it is preferred to firstly prepare a reference data of the through-hole portion under an oblique lighting condition, and then prepare a reference data of the remaining portion under the inspection lighting condition. In case of inspecting copper patterns, gold-plating patterns, solder-plating patterns or silk-printing patterns, having similar brightness, it is preferred to use different detecting conditions of color component or chromaticity in place of the different lighting conditions. In addition, it is possible to use different detecting conditions of polarization property or fluorescence property of an object to be inspected in place of the different lighting conditions.

When performing the image-taking operations with use of a plurality of reference patterns having variations, it is preferred to renew the reference data by adjusting a position of a second or later reference pattern according to a position of a specific pattern classification of a first reference pattern. It is possible to prevent deterioration of the pattern inspection accuracy.

When detecting the defect of the inspection pattern, it is preferred to adjust a position of the inspection pattern according to a position of a specific pattern classification of the reference pattern, and compare the inspection-image data with the reference data. In this case, it is possible to provide an accurate inspection even when there is a little position shift of the inspection pattern.

When determining the edge direction of the brightness step portion, it is preferred to compare a first pixel disposed in a rectangular direction of the pixel window with a second pixel disposed in an oblique direction of the pixel window, and determine the edge direction according to the first pixel when a pixel-value difference between the first and second pixels is smaller than a predetermined pixel value. It is possible to properly determine the edge direction irrespective of variations in pattern-edge brightness.

In this embodiment, although the present invention is explained as the method of inspecting patterns of a wiring board, the present invention may be applied to an article having patterns to be inspected. For example, when a printed article requires an aesthetic appearance, it is possible to perform the inspection while changing the inspection standard every color of multicolor printing pattern, or every line width/part position. In addition, When information about configuration or position of a thin, small portion such as a mark is important, it is possible to inspect the small portion according to a severe inspection standard and an average inspection standard. In addition, in case of inspecting defects such as scratch and contamination of an article having a pattern or mark, it is possible to perform the inspection while separating the pattern or mark design from the defects.

Thus, when an article to be inspected has a plurality pattern classifications, and it is desired to inspect the article according to an individual inspection standard every pattern classification, it is very effective to apply the pattern inspection method of the present invention which has capable of providing the following advantages.

1) it is possible to perform the pattern inspection while considering the kinds of defects and the inspecting condition.

2) it is possible to inspect only a desired region according to a severe inspection standard.

3) it is possible to prevent over-detection of defects.

What is claimed is:

1. A pattern inspection method comprising the steps of:

providing a plurality of pattern classifications according to pixel-value ranges of a reference-image data obtained from at least one reference pattern;

setting reference-data preparing parameters every pattern classification;

with respect to each of pixels of said reference-image data, comparing values of said pixel and required neighbor pixels defined around said pixel with said pixel-value ranges, so that 1) when said pixel and said neighbor pixels are included in a single pixel-value range, said pixel is decided as a uniform portion, and a reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications;

taking an image of a pattern to be inspected to obtain an inspection-image data; and comparing said inspection-image data with said reference data to detect a defect of said pattern;

wherein said reference-data preparing parameters comprises center-mask mode parameters having a center-mask mode value, upper-limit value and a lower limit value which are used to determine said reference data of said uniform portion, and wherein a method of preparing said reference data of said uniform portion using said center-mask mode parameters comprises at least one of a first set mode, in which said upper-limit and lower-limit values of said center-mask mode parameters are forcedly set on upper-limit and lower-limit reference values of said reference data irrespective of a previously-determined reference data, and a second set mode, in which said upper-limit and lower-limit values of said center-mask mode parameters are set on said upper-limit and lower-limit reference values of said reference data only when a range between said upper-limit and lower-limit values is larger than the range between upper-limit and lower-limit reference values of the previously-determined reference data.

2. A pattern inspection method comprising the steps of:

providing a plurality of pattern classifications according to pixel-value ranges of a reference-image data obtained from at least one reference pattern;

setting reference-data preparing parameters every pattern classification;

with respect to each of pixels of said reference-image data, comparing values of said pixel and required neighbor pixels defined around said pixel with said pixel-value ranges, so that 1) when said pixel and said neighbor pixels are included in a single pixel-value range, said pixel is decided as a uniform portion, and a reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications;

taking an image of a pattern to be inspected to obtain an inspection-image data; and comparing said inspection-image data with said reference data to detect a defect of said pattern;

wherein said reference-data preparing parameters comprises edge-mask mode parameters having an edge-mask mode value, upper-limit value and a lower-limit value which are used to determine said reference data of said step portion, and wherein a method of preparing said reference data of said step portion using said edge-mask mode parameters comprises a first set mode, in which said upper-limit and lower-limit values of said edge-mask mode parameters are set on upper-limit and lower-limit reference values of said reference data of said pixel decided as said step portion, and a second set mode, in which said upper-limit and lower-limit values of said edge-mask mode parameters are set on upper-limit and lower-limit reference values of said reference data of a pixel located around said pixel.

3. A pattern inspection method comprising the steps of:

providing a plurality of pattern classifications according to pixel-value ranges of a reference-image data obtained from at least one reference pattern;

setting reference-data preparing parameters every pattern classification;

with respect to each of pixels of said reference-image data, comparing values of said pixel and required neighbor pixels defined around said pixel with said pixel-value ranges, so that 1) when said pixel and said neighbor pixels are included in a single pixel-value range, said pixel is decided as a uniform portion, and a reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference data preparing parameters of at least one of said internal and external pattern classifications;

taking an image of a pattern to be inspected to obtain an inspection-image data; and comparing said inspection-image data with said reference data to detect a defect of said pattern;

wherein said reference-data preparing parameters comprises shift mode parameters having shift mode values, upper-limit acceptable value and a lower-limit acceptable value, wherein a method of preparing said reference data of said step portion using said shift mode parameters comprises at least one a first shift mode, in which an edge position of said step portion is shifted by a first shifting amount of 1 pixel or more in one of positive and negative directions, and a second shift mode, in which said edge position is shifted by a second shifting amount of less than 1 pixel in one of the positive and negative directions, and wherein a range between upper-limit and lower-limit reference values of the previously-determined reference data is renewed only when said range is expanded by at least one of an upper-limit correction value defined as a sum of said upper-limit acceptable value and a maximum pixel value obtained when said edge position is shifted by one of said first and second shifting amounts in a rectangular direction to an edge line, and a lower-limit correction value defined as a difference between said lower-limit acceptable limit and a minimum pixel value obtained when said edge position is shifted by one of said first and second shifting amounts in the rectangular direction to the edge line.

4. A pattern inspection method comprising the steps of:

providing a plurality of pattern classifications according to pixel-value ranges of a reference-image data obtained from at least one reference pattern;

setting reference-data preparing parameters every pattern classification;

with respect to each of pixels of said reference-image data, comparing values of said pixel and required neighbor pixels defined around said pixel with said pixel-value ranges, so that 1) when said pixel and said neighbor pixels are included in a single pixel-value range, said pixel is decided as a uniform portion, and a reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications;

taking an image of a pattern to be inspected to obtain an inspection-image data; and comparing said inspection-image data with said reference data to detect a defect of said pattern;

wherein said reference data is obtained by preparing a first reference data from a first reference-image data of a specific portion of said reference pattern detected under a first condition, preparing a second reference data from a second reference-image data of a remaining portion of said reference pattern detected under a second condition, and combining said first reference data with said second reference data.

5. The pattern inspection method as set forth in claim 3, wherein said reference-image data is obtained by the steps of:

taking images of a plurality of reference patterns to prepare image data;

adjusting positions of said image data; and performing an operation for determining one of an intermediate-value and an intermediate-mean value of said image data every pixel.

6. The pattern inspection method as set forth in claim 1, wherein said reference data of a specific region of said reference pattern has a specific-region number, and wherein when a decision of defect candidate is obtained by comparing said inspection-image data with said reference data having said specific-region number, a rechecking treatment is performed to cancel the decision of defect candidate when said inspection-image data is decided as good quality by said rechecking treatment.

7. The pattern inspection method as set forth in claim 6, wherein said rechecking treatment is performed according to a pixel-value fluctuation width.

8. The pattern inspection method as set forth in claim 6, wherein said rechecking treatment is performed according to a comparison with a good-quality decision pattern.

9. The pattern inspection method as set forth in claim 6, wherein said specific-region number is provided to said reference data of both of said uniform portion and said step portion with respect to a required pattern classification.

10. The pattern inspection method as set forth in claim 6, wherein said rechecking treatment is performed by shifting a portion of said reference data by a shifting amount to obtain a partially-corrected reference data, and comparing said inspection-image data with said partially corrected reference data.

11. The pattern inspection method as set forth in claim 6, wherein said rechecking treatment comprises the steps of:

detecting a position shift of said inspection-image data from said reference data;

preparing a partially corrected reference data by shifting a specific portion of said reference data by a shifting amount in a direction of said position shift, and setting a pixel-value acceptable width of said specific portion on a reference-data blank region caused in said reference data by the shifting; and comparing said inspection-image data with said partially corrected reference data.

12. A pattern inspection apparatus comprising:

an image-taking unit for taking images of a reference pattern and a pattern to be inspected to provide a reference-image data and an inspection-image data;

a first memory unit for storing said reference-image data and said inspection-image data;

a reference-data-preparing unit for preparing a reference data from said reference-image data;

a second memory unit for storing said reference data; and a defect-detecting unit for comparing said inspection-image data with said reference data to detect a defect of said pattern, wherein said reference-data preparing unit provides a plurality of pattern classifications according to pixel-value ranges of said reference-image data, and reference-data preparing parameters every pattern classification; with respect to each of pixels of said reference-image data, said reference-data preparing unit compares values of said pixel and required neighbor pixels defined around said pixel with said pixel-value ranges, so that 1) when the values of said pixel and said neighbor pixels are included in a single pixel-value range, said pixel is decided as a uniform portion, and said reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications, wherein said reference-data preparing parameters comprises center-mask mode parameters having a center-mask mode value, upper-limit value and a lower limit value which are used to determine said reference data of said uniform portion, and wherein said reference-data-preparing unit prepares said reference data of said uniform portion using said center-mask mode parameters according to a method comprising at least one of a first set mode, in which said upper-limit and lower-limit values of said center-mask mode parameters are forcedly set on upper-limit and lower-limit reference values of said reference data irrespective of a previously-determined reference data, and a second set mode, in which said upper-limit and lower-limit values of said center-mask model parameters are set on said upper-limit and lower-limit reference values of said reference data only when a range between said upper-limit and lower-limit values is larger than the range between upper-limit and lower-limit reference values of the previously-determined reference data.

13. A pattern inspection apparatus comprising:

an image-taking unit for taking images of a reference pattern and a pattern to be inspected to provide a reference-image data and an inspection-image data;

a first memory unit for storing said reference-image data and said inspection-image data;

a reference-data-preparing unit for preparing a reference data from said reference-image data;

a second memory unit for storing said reference data; and a defect-detecting unit for comparing said inspection-image data with said reference data to detect a defect of said pattern, wherein said reference-data preparing unit provides a plurality of pattern classifications according to pixel-value ranges of said reference-image data, and reference-data preparing parameters every pattern classification; with respect to each of pixels of said reference-image data, said reference-data preparing unit compares values of said pixel and required neighbor pixels defined around said pixel with said pixel-value ranges, so that 1) when the values of said pixel and said neighbor pixels are included in a single pixel-value range, said pixel is decided as a uniform portion, and said reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications, wherein said reference data preparing parameters comprises edge-mask mode parameters having an edge-mask mode value, upper-limit value and a lower-limit value which are used to determine said reference data of said step portion, and wherein said reference-data-preparing unit prepares said reference data of said step portion using said edge-mask mode parameters according to a method comprising a first set mode, in which said upper-limit and lower-limit values of said edge-mask mode parameters are set on upper-limit and lower-limit reference values of said reference data of said pixel decided as said step portion, and a second set mode, in which said upper-limit and lower-limit values of said edge-mask mod parameters are set on upper-limit and lower-limit reference values of said reference data of a pixel located around said pixel.

14. A pattern inspection apparatus comprising:

an image-taking unit for taking images of a reference pattern and a pattern to be inspected to provide a reference-image data and an inspection-image data;

a first memory unit for storing said reference-image data and said inspection-image data;

a reference-data-preparing unit for preparing a reference data from said reference-image data;

a second memory unit for storing said reference data; and a defect-detecting unit for comparing said inspection-image data with said reference data to detect a defect of said pattern, wherein said reference-data preparing unit provides a plurality of pattern classifications according to pixel-value ranges of said reference-image data, and reference-data preparing parameters every pattern classification; with respect to each of pixels of said reference-image data, said reference-data preparing unit compares values of said pixel and required neighbor pixels defined around said pixel with said pixel-value ranges, so that 1) when the values of said pixel and said neighbor pixels are included in a single pixel-value range, said pixel is decided as a uniform portion, and said reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications, wherein said reference-data preparing parameters comprises shift mode parameters having shift mode values, upper-limit acceptable value and a lower-limit acceptable value, wherein said reference-data-preparing unit prepares said reference data of said step portion using said shift mode parameters according to a method comprising at least one of a first shift mode, in which an edge position of said step portion is shifted by a first shifting amount of 1 pixel or more in one of positive and negative directions, and a second shift mode, in which said edge position is shifted by a second shifting amount of less than 1 pixel in one of the positive and negative directions, and wherein a range between upper-limit and lower-limit reference values of the previously-determined reference data is renewed only when said range is expanded by at least one of an upper-limit correction value defined as a sum of said upper-limit acceptable value and a maximum pixel value obtained when said edge position is shifted by one of said first and second shifting amounts in a rectangular direction to an edge line, and a lower-limit correction value defined as a difference between said lower-limit acceptable limit and a minimum pixel value obtained when said edge position is shifted by one of said first and second shifting amounts in the rectangular direction to the edge line.

15. A pattern inspection apparatus comprising:

an image-taking unit for taking images of a reference pattern and a pattern to be inspected to provide a reference-image data and an inspection-image data;

a first memory unit for storing said reference-image data and said inspection-image data;

a reference-data-preparing unit for preparing a reference data from said reference-image data;

a second memory unit for storing said reference data; and a defect-detecting unit for comparing said inspection-image data with said reference data to detect a defect of said pattern, wherein said reference-data preparing unit provides a plurality of pattern classifications according to pixel-value ranges of said reference-image data, and reference-data preparing parameters every pattern classification; with respect to each of pixels of said reference-image data, said reference-data preparing unit compares values of said pixel and required neighbor pixels defined around said pixel with said pixel-value ranges, so that 1) when the values of said pixel and said neighbor pixels are included in a single pixel-value range, said pixel is decided as a uniform portion, and said reference data of said pixel is prepared according to said reference-data preparing parameters of said pattern classification corresponding to said single pixel-value range, and 2) when at least one of said neighbor pixels is included in a different pixel-value range from said pixel, said pixel is decided as a step portion, and internal and external pattern classifications of said step portion are determined, so that said reference data of said pixel is prepared according to said reference-data preparing parameters of at least one of said internal and external pattern classifications, wherein said reference-data-preparing unit prepares said reference data by preparing a first reference data from a first reference-image data of a specific portion of said reference pattern detected under a first condition, preparing a second reference data from a second reference-image data of a remaining portion of said reference pattern detected under a second condition, and combining said first reference data with said second reference data.

* * * * *

UNITED STATES PATENT AND TRADEMARK OFFICE
CERTIFICATE OF CORRECTION

PATENT NO. : 6,222,935 B1
DATED : April 24, 2001
INVENTOR(S) : Shinji Okamoto

It is certified that error appears in the above-identified patent and that said Letters Patent is hereby corrected as shown below:

Please change the following:

(22)     PCT Filed:     "January 14, 1999" to -- June 25, 1998 -- .

Signed and Sealed this

Twenty-eighth Day of August, 2001

*Attest:*

NICHOLAS P. GODICI
*Attesting Officer*     *Acting Director of the United States Patent and Trademark Office*